(12) United States Patent
Ikuta et al.

(10) Patent No.: US 8,263,334 B2
(45) Date of Patent: Sep. 11, 2012

(54) METHOD OF NUCLEIC ACID SEQUENCE DETECTION AND NUCLEIC ACID SEQUENCE DETECTION SUBSTRATE

(75) Inventors: Hajime Ikuta, Tokyo (JP); Kiyokazu Takemura, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 0 days.

(21) Appl. No.: 13/064,322

(22) Filed: Mar. 18, 2011

(65) Prior Publication Data

US 2011/0190158 A1 Aug. 4, 2011

Related U.S. Application Data

(62) Division of application No. 12/289,512, filed on Oct. 29, 2008.

(30) Foreign Application Priority Data

Nov. 5, 2007 (JP) ................................ 2007-286874

(51) Int. Cl.
*C12Q 1/68* (2006.01)
*C12P 19/34* (2006.01)
*C07H 21/02* (2006.01)
*C07H 21/00* (2006.01)
*C07H 21/04* (2006.01)

(52) U.S. Cl. ...... 435/6.1; 435/6.19; 435/91.1; 435/91.2; 536/22.1; 536/23.1

(58) Field of Classification Search .................. 435/6.1, 435/6.19, 91.1, 91.2; 536/22.1, 23.1
See application file for complete search history.

(56) References Cited

U.S. PATENT DOCUMENTS

| | | | | |
|---|---|---|---|---|
| 5,314,809 A | * | 5/1994 | Erlich et al. ................. | 435/91.2 |
| 5,641,658 A | * | 6/1997 | Adams et al. ................ | 435/91.2 |
| 5,679,524 A | | 10/1997 | Nikiforov et al. | |
| 2002/0098526 A1 | * | 7/2002 | Bamdad ....................... | 435/7.9 |
| 2002/0150900 A1 | * | 10/2002 | Marshall et al. .............. | 435/6 |
| 2003/0215821 A1 | | 11/2003 | Gunderson et al. | |

FOREIGN PATENT DOCUMENTS

| | | |
|---|---|---|
| EP | 1 634 963 A1 | 3/2006 |
| JP | A-2006-174788 | 7/2006 |
| JP | A-2007-222010 | 9/2007 |
| WO | WO 01/62982 A2 | 8/2001 |
| WO | WO 02/46456 A1 | 6/2002 |
| WO | WO 03/076902 A2 | 9/2003 |

OTHER PUBLICATIONS

Pubmed search results down loaded from the internet [http://www.ncbi.nlm.nih.gov/pubmed?term=coull], pp. 1 and 2, printed on Oct. 14, 2011.*
Kinoshita et al., "Multiple Primer Extension by DNA Polymerase on a Novel Plastic DNA Array Coated with a Biocompatible Polymer", Nucleic Acids Research, vol. 35, No. 1, pp. 1-9.
Collins et al., "A Branched DNA Signal Amplification Assay for Quantification of Nucleic Acid Targets Below 100 Molecules/ml," Nucleic Acids Research, vol. 25, No. 15, pp. 2979-2984, 1997.
Tsai et al., "Nucleic Acid Capture Assay, A New Method for Direct Quantitation of Nucleic Acids," Nucleic Acids Research, vol. 31, No. 6, pp. 1-7, 2003.
Jan. 28, 2010 European Office Action issued in corresponding European Application No. 08 019 285.9-1222.
Apr. 26, 2011 Office Action issued in U.S. Appl. No. 12/289,512.
Oct. 14, 2011 Office Action issued in U.S. Appl. No. 12/289,512.

* cited by examiner

*Primary Examiner* — Stephen Kapushoc
*Assistant Examiner* — Narayan Bhat
(74) *Attorney, Agent, or Firm* — Oliff & Berridge, PLC

(57) ABSTRACT

According to an aspect of the present invention, a pair of oligonucleotide strands are anchored onto the surface of a substrate by immobilizing one of the ends thereof onto the substrate. Each of the immobilized oligonucleotide strands is bound to a target nucleic acid sequence (single-stranded) having complementary sequences thereto to form a cross-linked structure on the substrate, thereby forming a finely reticulated space. Ligands are captured by this reticulated space through physical adsorption and caused to color with active substances reactive to the ligands. As a result of this, the present invention is capable of highly sensitively detecting even an exceedingly small concentration of a particular target nucleic acid sequence to be detected, at low cost and for a short time.

17 Claims, 10 Drawing Sheets

(TABLE 1)

|  | S/N RATIO: (S+N)/N |
|---|---|
| G1 PCR PRODUCT | 0.97 |
| G2 PCR PRODUCT | 0.98 |

METHOD OF NUCLEIC ACID SEQUENCE DETECTION AND NUCLEIC ACID SEQUENCE DETECTION SUBSTRATE

CROSS-REFERENCE TO PRIOR APPLICATION

This is a divisional of application Ser. No. 12/289,512 filed Oct. 29, 2008, and claims the benefit of Japanese Patent Application No. 2007-286874 filed Nov. 5, 2007. The entire disclosures of the prior applications are hereby incorporated by reference in their entirety.

BACKGROUND OF THE INVENTION

1. Field of the Invention

The present invention relates to a method of nucleic acid sequence detection and a nucleic acid sequence detection substrate. Particularly, the present invention relates to a technique for highly sensitively detecting, conveniently and at low cost, the presence of a particular target nucleic acid sequence to be detected in a sample.

2. Description of the Related Art

A conventional method for detecting a nucleic acid sequence specific to a sample as a target involves: binding the target nucleic acid sequence to oligonucleotide strands immobilized on a substrate and binding a different oligonucleotide strand labeled with a fluorescent substance to the bound target nucleic acid sequence; and detecting the presence of the particular nucleic acid sequence in the sample by detecting/amplifying a reflected light signal from the fluorescent substance label by irradiation with light (e.g., laser beam) at a particular wavelength. Another detection method involves: binding the target nucleic acid sequence to oligonucleotide strands immobilized on a substrate; performing elongation reaction using the oligonucleotide strands as primers and the bound target nucleic acid sequence as a template, wherein base substances incorporated during the reaction are labeled with a fluorescent substance; and detecting/amplifying a reflected light signal from the fluorescent substance label by irradiation with light (e.g., laser beam) at a particular wavelength.

However, these detection methods must detect a fluorescent substance and therefore require a special detection apparatus that emits light at a particular wavelength. Such a detection apparatus is expensive and has a limited use to some research institutes or universities under the present circumstances. Thus, these approaches cannot be adopted, for example, for conveniently detecting pathogenic microorganisms such as norovirus or *Cryptosporidium* in water (sample) at water treatment sites, due to complicated procedures and expensive analysis apparatuses.

Against this backdrop, for example, the MPEX (Multiple Primer EXtension) method described in K. Kinoshita et al., Multiple primer extension by DNA polymerase on a novel plastic DNA array coated with a biocompatible polymer, Nucleic Acid Research, Vol. 35, No. 1, 2007, pp. e3, and Japanese Patent Application Laid-Open Nos. 2006-174788 and 2007-222010 has been developed as a method for conveniently detecting a particular nucleic acid sequence at detection (e.g., water treatment sites) at low cost.

This MPEX method is a genetic testing method using DNA elongation reaction catalyzed by an enzyme (DNA polymerase) on a substrate and is also used in gene mutation analysis, SNP (Single Nucleotide Polymorphism) analysis, and microorganism identification. This method uses, as primers, oligonucleotide strands immobilized on a substrate having, on the surface thereof, a polymer substance containing a first unit having a group induced from phosphoric ester constituting the hydrophilic moiety of phospholipid and a second unit having an active ester group. It involves: after addition of a target nucleic acid sequence, heat-denaturing the double-stranded DNA into single strands on the substrate and performing DNA elongation reaction catalyzed by DNA polymerase using the single strand as a template to incorporate bases, all or some of which are modified with a ligand, into the elongation reaction product (amplified DNA); and finally adding thereto an active substance reactive to the ligand for reaction. The MPEX method thus achieves highly sensitive gene detection.

SUMMARY OF THE INVENTION

However, coloring dyes are inferior in sensitivity of detection signal amplification to fluorescent substances. Therefore, the MPEX method fails to highly sensitively detect, for example, pathogenic microorganisms such as norovirus or *Cryptosporidium*, which are present only with a very low order in water (sample) and cannot be proliferated by culture.

The MPEX method requires, for highly sensitive detection, increasing the amount of labels and requires, for this purpose, the step of increasing the concentration of a target nucleic acid sequence by PCR or the like. Therefore, this method disadvantageously takes long time to obtain results.

Thus, the MPEX method must be further improved for detecting pathogenic microorganisms such as norovirus or *Cryptosporidium*, which are present only with a very low order in water and cannot be proliferated by culture.

Alternatively, even the use of fluorescent substances results in unstable detection sensitivity for an exceedingly small amount of a particular gene to be detected, as in the pathogenic microorganisms. Thus, precise detection cannot be achieved.

In consideration of such circumstances, an object of the present invention is to provide a method of nucleic acid sequence detection, which is capable of highly sensitively detecting even an exceedingly small concentration of a particular target nucleic acid sequence to be detected, at low cost and for a short time, and to provide a nucleic acid sequence detection substrate using the method.

A first aspect of the present invention for attaining the object provides a method of nucleic acid sequence detection for detecting the presence of a particular target nucleic acid sequence to be detected in a sample, the method comprising: an immobilization step of anchoring oligonucleotide strands onto a substrate by immobilizing one of the 5'- and 3'-ends thereof onto the substrate; a reticulated space formation step of performing, based on a set of the oligonucleotide strands, the immobilization step and binding the oligonucleotide strands to their respective complementary portions of the target nucleic acid sequence to form a cross-linked structure on plural sets to form a finely reticulated space on the substrate, wherein a plurality of the cross-linked structures are intertwined with each other; a capture step of capturing a ligand by the reticulated space through physical adsorption; a coloring step of causing the captured ligand to color with an active substance reactive to the ligand; and a detection step of detecting a color signal derived from the coloring to detect the target nucleic acid sequence.

In this context, the target nucleic acid sequence refers to RNA or DNA having a nucleotide sequence to be detected.

According to the first aspect of the present invention, a pair of oligonucleotide strands are anchored onto the surface of a substrate by immobilizing one of the ends thereof onto the substrate. Each of the immobilized oligonucleotide strands is bound to the target nucleic acid sequence (single-stranded) having complementary sequences thereto to form a cross-linked structure on the substrate, thereby forming a finely reticulated space. Ligands are captured by this reticulated space through physical adsorption and caused to color with active substances reactive to the ligands.

As described above, when the particular target nucleic acid sequence to be detected is present in the sample, a reticulated space is formed on the substrate, and a ligand as a constituent of a chromogenic substance for coloring is captured by this reticulated space through physical adsorption. Therefore, the chromogenic substance can be captured at a high concentration by the reticulated space by adding thereto a ligand-reactive active substance as another constituent of the chromogenic substance. This achieves highly sensitive detection even for an exceedingly small concentration of a particular target nucleic acid sequence to be detected. Moreover, the first aspect of the present invention requires no elongation reaction and can therefore take short time for detection. Furthermore, the first aspect of the present invention can use coloring dyes, not fluorescent dyes, and can therefore eliminate the need of expensive detection apparatuses, leading to detection at low cost.

In this context, information about the target nucleic acid sequence can be obtained, for example, on the Internet, using DNA data banks (e.g., DDBJ (DNA Data Bank of Japan), EMBL (European Molecular Biology Laboratory), and GenBank). Thus, two nucleic acid sequences specific to a sample may be respectively assigned to a pair of the oligonucleotide strands by identifying these two specific sites in the target nucleic acid sequence.

A second aspect of the present invention for attaining the object provides a method of nucleic acid sequence detection for detecting the presence of a particular target nucleic acid sequence to be detected in a sample, the method comprising: immobilizing plural sets of oligonucleotide strands onto a substrate; adding, to a reaction system, the sample containing the target nucleic acid sequence as well as a ligand as a constituent of a chromogenic substance and setting the temperature of the reaction system to a temperature at which the target nucleic acid sequence is heat-denatured into single strands; setting the temperature of the reaction system to a hybridization temperature at which the oligonucleotide strands complementarily bind to the target nucleic acid sequence; adding, onto the substrate, an active substance as another constituent of the chromogenic substance for reaction with the ligand; and detecting a color signal derived from coloring by the chromogenic substance.

The second aspect of the present invention interprets the invention based on operational procedures, whereas the first aspect interprets the invention based on a mechanism.

According to the second aspect, a pair of oligonucleotide strands are designed such that each of them has a complementary sequence portion to the target nucleic acid sequence heat-denatured into single strands. Therefore, in the reaction system containing a ligand as a constituent of a chromogenic substance, a plurality of the cross-linked structures shown in the first aspect are formed through hybridization reaction. Then, a plurality of the ligands are captured by the cross-linked structures through physical adsorption. This can produce a strong color signal, leading to highly sensitive detection.

A third aspect of the present invention for attaining the object provides a method of nucleic acid sequence detection for detecting the presence of a particular target nucleic acid sequence to be detected in a sample, the method comprising: a design step of designing first and second oligonucleotide strands in advance such that the second oligonucleotide strand has a complementary nucleic acid sequence to an elongation reaction product dissociated from a duplex formed through elongation reaction using the first oligonucleotide strand as a primer and the target nucleic acid sequence as a template after complementary binding of the target nucleic acid sequence and the first oligonucleotide strand; an immobilization step of anchoring the first and second oligonucleotide strands onto a substrate by immobilizing the 5'-ends thereof onto the substrate; a first elongation reaction step of complementarily binding the first oligonucleotide strand to the target nucleic acid sequence and performing first elongation reaction using the first oligonucleotide strand as a primer and the target nucleic acid sequence as a template; a first dissociation step of dissociating, from the target nucleic acid sequence, the first elongation reaction product extended in the first elongation reaction step; a first cross-linking step of binding the dissociated first elongation reaction product to the second oligonucleotide strand to form a cross-linked structure between the first and second oligonucleotide strands; a second elongation reaction step of performing second elongation reaction using the second oligonucleotide strand as a primer and the first elongation reaction product as a template; a second dissociation step of dissociating therefrom the second elongation reaction product extended in the second elongation reaction step; a second cross-linking step of performing the first elongation reaction step to the second dissociation step on a plurality of the first and second oligonucleotide strands and binding a first oligonucleotide strand different from the first oligonucleotide strand to the dissociated second elongation reaction product to form a cross-linked structure between the second and first oligonucleotide strands; a repetitive cross-linking step of repeating the first and second cross-linking steps between a plurality of the first and second oligonucleotide strands; a reticulated space formation step of forming a finely reticulated space by the repetitive cross-linking step, wherein a plurality of the cross-linked structures are intertwined with each other; a capture step of capturing a ligand by the reticulated space through physical adsorption; a coloring step of causing the captured ligand to color with an active substance reactive to the ligand; and a detection step of detecting a color signal derived from the coloring to detect the target nucleic acid sequence.

According to the third aspect of the present invention, a reticulated space is formed by a method different from that in the first aspect. Specifically, according to the third aspect, a first oligonucleotide strand anchored on the surface of a substrate by the 5'-end thereof is complementarily bound to the target nucleic acid sequence. Then, a first duplex is dissociated, which is formed through elongation reaction using the first oligonucleotide strand as a primer and the target nucleic acid sequence as a template such that the first duplex has a complementary nucleic acid sequence to the target nucleic acid sequence. Then, the first elongation reaction product dissociated therefrom is complementarily bound to a second oligonucleotide strand anchored on the surface of the substrate by one end. Then, a second duplex is formed through elongation reaction using the second oligonucleotide strand as a primer and the first elongation reaction product as a template. The second elongation reaction product is dissociated from the first duplex.

This can form a plurality of cross-linked structures of nucleic acid sequences through elongation and dissociation reactions on the substrate. The plurality of the cross-linked structures can be intricately intertwined with each other, thereby forming a reticulated space on the substrate.

In this context, information about the target nucleic acid sequence can be obtained, for example, on the Internet, using DNA data banks (e.g., DDBJ (DNA Data Bank of Japan), EMBL (European Molecular Biology Laboratory), and GenBank). Thus, a nucleic acid sequence specific to a sample is identified in the target nucleic acid sequence and assigned to the first oligonucleotide strand. Moreover, the second oligonucleotide strand is designed such that it has a complementary nucleic acid sequence to a first elongation reaction product. According to the third aspect, the first and second oligonucleotide strands are designed such that they have different nucleic acid sequences.

Moreover, according to the third aspect, ligands are captured by the reticulated space through physical adsorption and caused to color with active substances reactive to the ligands. As described above, when the particular target nucleic acid sequence to be detected is present in the sample, a reticulated space is formed on the substrate, and a ligand as a constituent of a chromogenic substance for coloring is captured by this reticulated space through physical adsorption. Therefore, the chromogenic substance can be captured at a high concentration by the reticulated space by adding thereto an active substance reactive to the ligand. This achieves highly sensitive detection even for an exceedingly small concentration of a particular target nucleic acid sequence to be detected. Moreover, the amount of a color signal does not largely depend on an elongation reaction level. The third aspect of the present invention can therefore take short time for detection. Furthermore, the third aspect of the present invention can eliminate the need of expensive detection apparatuses, leading to detection at low cost.

A fourth aspect of the present invention provides the method of nucleic acid sequence detection according to the third aspect, further comprising: a third elongation reaction step of binding the second elongation reaction product dissociated in the second dissociation step to a third oligonucleotide strand designed such that the third oligonucleotide strand has a complementary nucleic acid sequence to the second elongation reaction product and performing third elongation reaction using the third oligonucleotide strand as a primer and the second elongation reaction product as a template; a third dissociation step of dissociating, from the second elongation reaction product, the third elongation reaction product extended in the third elongation reaction step; a third cross-linking step of binding a first oligonucleotide strand different from the first oligonucleotide strand to the dissociated third elongation reaction product to form a cross-linked structure between the third and first oligonucleotide strands; and a repetitive cross-linking step of repeating the first, second, and third cross-linking steps between a plurality of the first, second, and third oligonucleotide strands.

The fourth aspect uses three oligonucleotide strands. A reticulated space can be formed using dissociated elongation reaction products one after another by repeating binding→elongation→dissociation reactions. The fourth aspect of the present invention therefore achieves highly sensitive detection even for a smaller concentration of a target nucleic acid sequence. Moreover, if the first oligonucleotide strand fails to bind to the target nucleic acid sequence, reaction can proceed by the binding of the third oligonucleotide strand instead. Therefore, detection sensitivity can be stabilized. According to the fourth aspect, which uses three oligonucleotide strands, four or more oligonucleotide strands are more preferable. Thus, the number of designed oligonucleotide strands can be increased according to the concentration of the target nucleic acid sequence present in the sample (i.e., when the target nucleic acid sequence present in the sample has a small concentration), leading to more highly sensitive detection.

A fifth aspect of the present invention provides the third or fourth aspect further comprising a hybridization step of setting the temperature after the repetitive cross-linking step to a hybridization temperature for the oligonucleotide strands.

As a result, uncrosslinked elongation reaction products after the repetitive cross-linking step are bound to the oligonucleotide strands anchored on the substrate by the 5'-ends thereof to form a larger number of cross-linked structures. The plurality of the cross-linked structures can be intricately intertwined with each other, leading to more highly sensitive detection.

A sixth aspect of the present invention interprets the invention based on operational procedures, whereas the third aspect interprets the invention based on a mechanism.

A seventh aspect of the present invention provides any of the first to sixth aspects, wherein the ligand is one member selected from the group consisting of biotin, avidin, antigens, antibodies, hapten, oligonucleotides, and enzymes.

The seventh aspect lists preferable specific examples of the ligand.

An eighth aspect of the present invention provides any of the first to sixth aspects, wherein the ligand is one member selected from the group consisting of biotinylated enzymes, avidinylated enzymes, streptavidinylated enzymes, enzyme labels, and enzyme-labeled oligonucleotides.

The eighth aspect lists alternative preferable specific examples of the ligand.

A ninth aspect of the present invention provides any of the first to eighth aspects, wherein the active substance is one member selected from the group consisting of enzyme-labeled receptors, fluorescent substance-labeled receptors, and substrates.

The ninth aspect lists preferable specific examples of the active substance.

A tenth aspect of the present invention provides any of the first to ninth aspects, wherein the substrate has, on the surface thereof, a layer comprising a hydrophilic polymer as well as a functional group reactive to an amino group.

According to the tenth aspect, this can suppress non-specific binding of the oligonucleotide strands and firmly immobilize the oligonucleotide strands onto the substrate.

An eleventh aspect of the present invention for attaining the object provides a nucleic acid sequence detection substrate for performing a method of nucleic acid sequence detection according to any of the first to tenth aspects, wherein oligonucleotide strands are spotted on the substrate.

According to the eleventh aspect, a sample for detecting a target nucleic acid sequence can be spotted (added dropwise) to the nucleic acid sequence detection substrate of the present invention and reacted, thereby highly sensitively detecting, by visual observation, the presence of the particular target nucleic acid sequence to be detected in the sample.

As described above, the method of nucleic acid sequence detection and the nucleic acid sequence detection substrate according to the present invention are capable of highly sensitively detecting even an exceedingly small concentration of a particular target nucleic acid sequence to be detected, at low cost and for a short time.

BRIEF DESCRIPTION OF THE DRAWINGS

FIGS. 7A to 7C are diagrams for illustrating color images derived from coloring on a substrate in Example;

FIG. 8 is a table for showing an average S/N ratio of results of digitizing color images in Example 1.

DETAILED DESCRIPTION OF THE PREFERRED EMBODIMENTS

Hereinafter, preferred embodiments of a method of nucleic acid sequence detection and a nucleic acid sequence detection substrate according to the present invention will be described in detail according to the accompanying drawings.

[First Embodiment of the Present Invention]

Figure 1A:
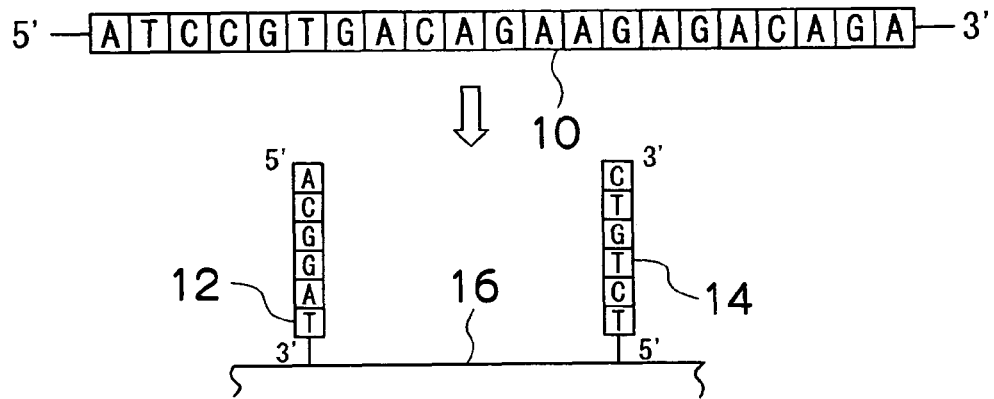
FIGS. 1A to 1C are diagrams for schematically showing the mechanism of a first embodiment of a method of nucleic acid sequence detection of the present invention using the target nucleic acid sequence 10 (SEQ ID NO:1)
Figure 1B:
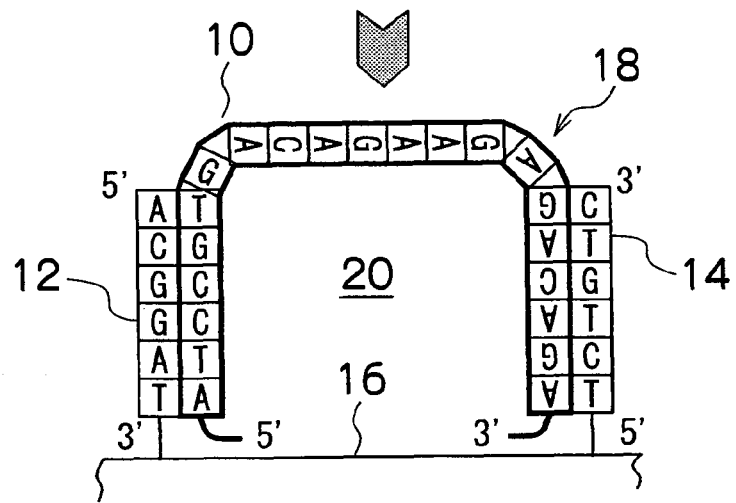
Figure 1C:
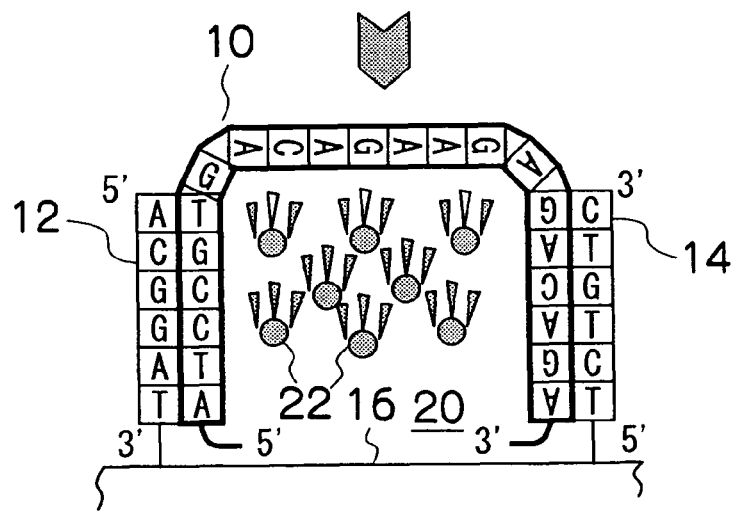

FIGS. 1A to 1C are diagrams for schematically showing the mechanism of a first embodiment of a method of nucleic acid sequence detection of the present invention.

In the diagrams, A, C, G, and T represent bases constituting nucleic acid sequences (i.e., A: adenine, C: cytosine, G: guanine, and T: thymine).

The first embodiment of the method of nucleic acid sequence detection of the present invention mainly comprises design, immobilization, cross-linking, reticulated space formation, capture, coloring, and detection steps.

The nucleic acid sequences of a pair of oligonucleotide strands 12 and 14 are designed in advance such that a target nucleic acid sequence (e.g., target DNA) 10 to be detected in a sample is cross-linked with the oligonucleotide strands 12 and 14 (design step). In this context, the target nucleic acid sequence 10 to be cross-linked refers to a nucleic acid sequence heat-denatured into single strands from a double strand.

Specifically, the nucleic acid sequence of the target nucleic acid sequence 10 to be detected is examined in advance, for example, on the Internet, from information stored in DNA data banks. The nucleic acid sequences of a pair of the oligonucleotide strands 12 and 14 are designed such that two sites in the nucleic acid sequence respectively complementarily bind to a pair of the oligonucleotide strands 12 and 14.

The oligonucleotide strand 12 shown on the left side in FIG. 1A has a nucleic acid sequence 3'-TAGGCA-5' (SEQ ID NO:2) starting from the substrate 16 side, which is designed to be complementary to a sequence portion 5'-ATCCGT-3' (SEQ ID NO:3) at one end of the target nucleic acid sequence 10. Alternatively, the oligonucleotide strand 14 shown on the right side in FIG. 1A has a nucleic acid sequence 5'-TCT-GTC-3' (SEQ ID NO:4) starting from the substrate 16 side, which is designed to be complementary to a sequence portion 3'-AGACAG-5' (SEQ ID NO:5) at the other end of the target nucleic acid sequence 10. Specifically, nucleic acid sequences respectively complementary to two sites in the target nucleic acid sequence 10 are respectively assigned to a pair of the oligonucleotide strands 12 and 14. The designed oligonucleotide strands 12 and 14 are preferably 6 to 30 bases long.

To design the oligonucleotide strands 12 and 14, nucleic acid sequences specific to the target nucleic acid sequence 10 are selected for the oligonucleotide strands 12 and 14 to prevent a pair of the oligonucleotide strands 12 and 14 from binding to nucleic acid sequences (e.g., animal, plant, or human DNA) other than the target nucleic acid sequence 10 contained in the sample.

A pair of the oligonucleotide strands 12 and 14 may have the same nucleic acid sequences or may have different nucleic acid sequences. Two sites in the target nucleic acid sequence 10 respectively matched with the oligonucleotide strands 12 and 14 must be distant from each other such that the target nucleic acid sequence 10 is capable of forming a cross-link with a pair of the oligonucleotide strands 12 and 14. However, these two sites do not have to be located at both ends of the target nucleic acid sequence 10.

Next, as shown in FIG. 1A, a pair of the oligonucleotide strands 12 and 14 are anchored onto the substrate 16 by immobilizing one of the 5'- and 3'-ends thereof onto the substrate 16 (immobilization step). FIG. 1A shows only a pair of the oligonucleotide strands 12 and 14. In actuality, plural sets of the pair of the oligonucleotide strands 12 and 14 are anchored on the substrate 16. In this context, the plural sets of the pair of the oligonucleotide strands 12 and 14 do not mean that the oligonucleotide strands 12 and 14 are quantitatively completely equal to each other.

The sample containing the target nucleic acid sequence 10 is spotted (added dropwise) onto the substrate 16 thus prepared to perform the cross-linking to detection steps. Specifically, as shown in FIG. 1B, a pair of the oligonucleotide strands 12 and 14 bind to their respective complementary portions of the target nucleic acid sequence 10 to form a cross-linked structure 18.

In this cross-linking step, nucleic acid sequences other than the target nucleic acid sequence 10 contained in the sample neither have a complementary relationship with a pair of the oligonucleotide strands 12 and 14 nor form the cross-linked structure 18.

Figure 2:
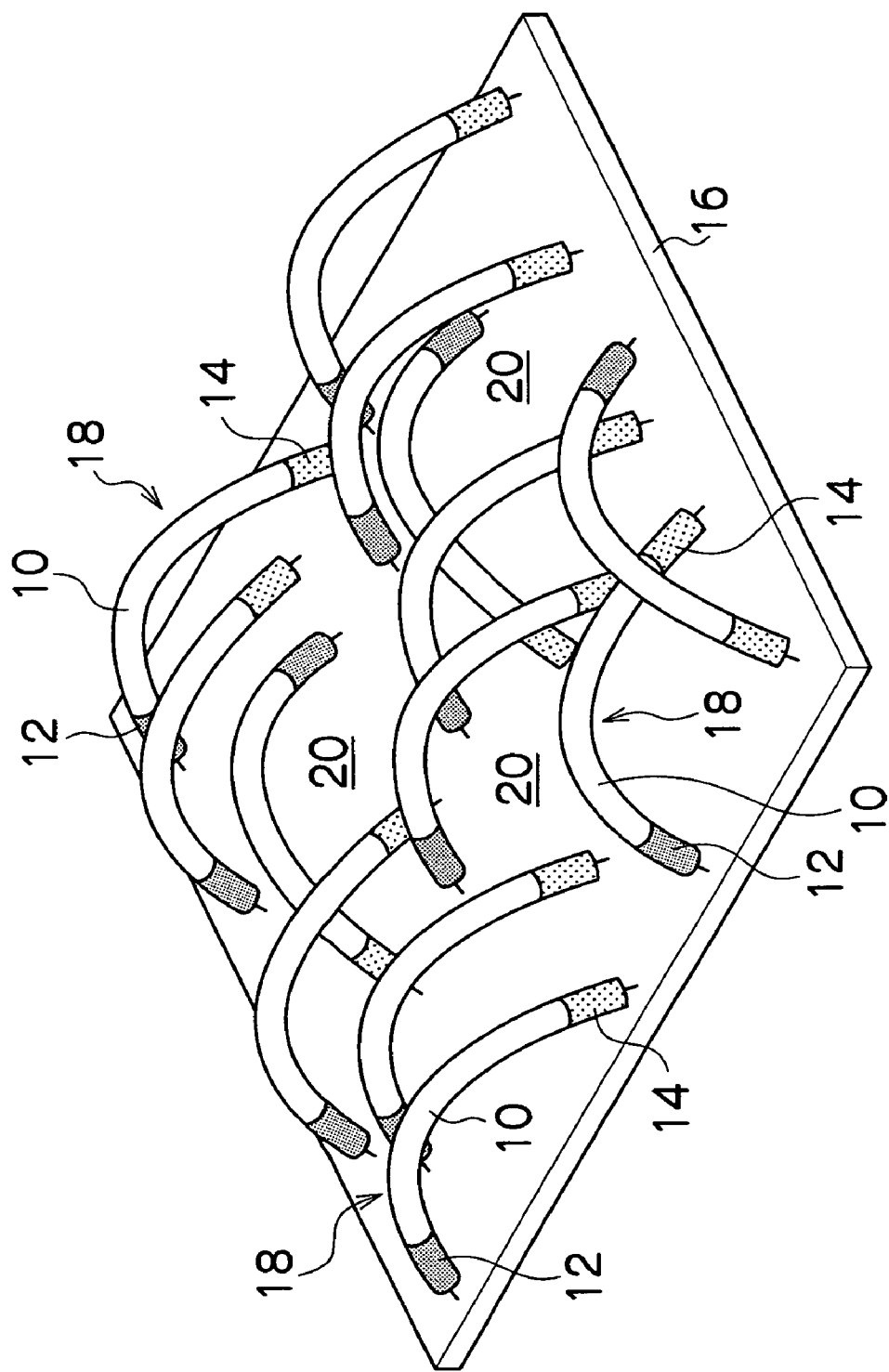
FIG. 2 is a diagram for schematically showing a reticulated space formed in the first embodiment of the present invention.

The cross-linking step is performed on plural sets of this pair of the oligonucleotide strands 12 and 14 to form, as shown in FIG. 2, a finely reticulated space 20 on the substrate 16, wherein a plurality of the cross-linked structures 18 are intricately intertwined with each other (reticulated space formation step). To facilitate understanding, FIG. 2 shows a simplified diagram of the reticulated space 20. In actuality, the cross-linked structures 18 are intricately intertwined with each other to form a high-density reticulated space 20. The formation of the reticulated space 20 can presumably be confirmed directly, for example, using an electron microscope. Alternatively, a pair of the oligonucleotide strands 12 and 14 may also be designed such that their nucleic acid sequences have small complementarity to the target nucleic acid sequence 10. As a result, a small color signal is obtained in the coloring step, and no color signal is obtained by eliminating any one of the oligonucleotide strands. Therefore, the formation of the reticulated space 20 can be confirmed indirectly.

As shown in FIG. 1C, a plurality of ligands 22 as a constituent of a chromogenic substance can be captured by this reticulated space 20 through physical adsorption (capture step). To facilitate understanding, FIG. 1C shows one cross-linked structure 18. In actuality, the ligands 22 are captured through physical adsorption by the reticulated space 20 wherein a plurality of the cross-linked structures 18 are intricately intertwined with each other, as shown in FIG. 2. In this context, the physical adsorption is based on the phenomenon in which small chemicals are easily trapped in small holes. Thus, the physical adsorption, unlike specific binding between particular chemicals, means non-specific action.

Thus, a plurality of the captured ligands 22 are caused to color with ligand 22-reactive active substances (not shown) as another constituent of the chromogenic substance (coloring step). Highly sensitive detection can be performed by detecting a color signal derived from the coloring. The color signal can be detected conveniently not only using general apparatuses such as an absorbance detector or image scanner but by visual observation through visualization with coloring dyes.

The ligand 22 that can be used preferably is one member selected from the group consisting of biotin, avidin, antigens, antibodies, hapten, oligonucleotides, and enzymes. Alternatively, the ligand 22 that can be used is one member selected from the group consisting of biotinylated enzymes, avidinylated enzymes, streptavidinylated enzymes, enzyme labels, and enzyme-labeled oligonucleotides. The active substance that can be used preferably is one member selected from the group consisting of enzyme-labeled receptors, fluorescent substance-labeled receptors, and substrates.

The coloring step will be described by taking, as an example, biotin used as a ligand and alkaline phosphatase-labeled avidin used as an active substance reactive to the ligand. Biotin reacts with avidin (biotin-avidin reaction) to specifically form a strong bond. Thus, biotin is captured by the reticulated space 20 and reacted with alkaline phosphatase-labeled avidin to bind plural alkaline phosphatase (AP) labels to the biotin. Avidin and biotin bind at a ratio of 1:4. Then, the alkaline phosphatase reacts with a substrate BCIP/NBT (BCIP/NBT reaction) to produce a bluish-purple color, which is in turn detected.

BCIP: 5-bromo-4-chloro-3-indolyl phosphate
NBT: nitroblue tetrazolium

Thus, as in the present invention, biotin as the ligand 22 is captured in a large amount by the reticulated space 20 to amplify biotin-avidin reaction and BCIP/NBT reaction against alkaline phosphatase, thereby forming a strong color signal.

In another method, digoxigenin (DIG), a cardiac glycoside obtained from a medicinal plant digitalis, may be used instead of biotin. In this case, digoxigenin immune-reacts with an alkaline phosphatase-labeled anti-digoxigenin antibody. The alkaline phosphatase can produce a bluish-purple color using BCIP/NBT, as in biotin, leading to highly sensitive detection.

Preferably, the substrate 16 used in the embodiments of the present invention has, on the surface thereof, a layer comprising a hydrophilic polymer as well as a functional group reactive to an amino group. The layer comprising a hydrophilic polymer mainly plays a role in suppressing non-specific binding of the oligonucleotide strands. The functional group reactive to an amino group plays a role in chemically immobilizing the oligonucleotide strands onto the substrate. Particularly, the oligonucleotide strands are firmly immobilized on the surface of the substrate 16 through covalent bonds at the functional group reactive to an amino group.

Examples of the hydrophilic polymer used in the present embodiment include polymer substances having a hydrophilic group in the main or side chain. Those containing, in the structure, any of polyalkylene oxide, polyethylene oxide, polypropylene oxide, polyacrylamide, and copolymers thereof are preferable. Particularly, a polyacrylamide gel is preferable, which has a reticulated structure in which polyacrylamide is three-dimensionally photocrosslinked with a photocrosslinking compound or the like.

Examples of the functional group reactive to an amino group used in the present embodiment include aldehyde and active ester groups. The active ester group is preferable. The active ester group is carboxylic acid having an activated carboxyl group and is carboxylic acid having a leaving group via C=O. Examples of the activated carboxylic acid derivative include compounds obtained by converting a carboxyl group of carboxylic acid such as acrylic acid, methacrylic acid, crotonic acid, maleic acid, or fumaric acid to acid anhydride, acid halide, active ester, or activated amide. For example, the active ester group is preferably a p-nitrophenyl ester, N-hydroxysuccinimide ester, succinimide ester, phthalimide ester, or 5-norbornene-2,3-dicarboxylmide ester group, more preferably a p-nitrophenyl ester or N-hydroxysuccinimide ester group.

The functional group reactive to an amino group may be introduced directly to the surface of the substrate or may be carried by the main or side chain of the hydrophilic polymer structure.

(Operational Procedures of Performing Detection Method of First Embodiment)

Figure 3:
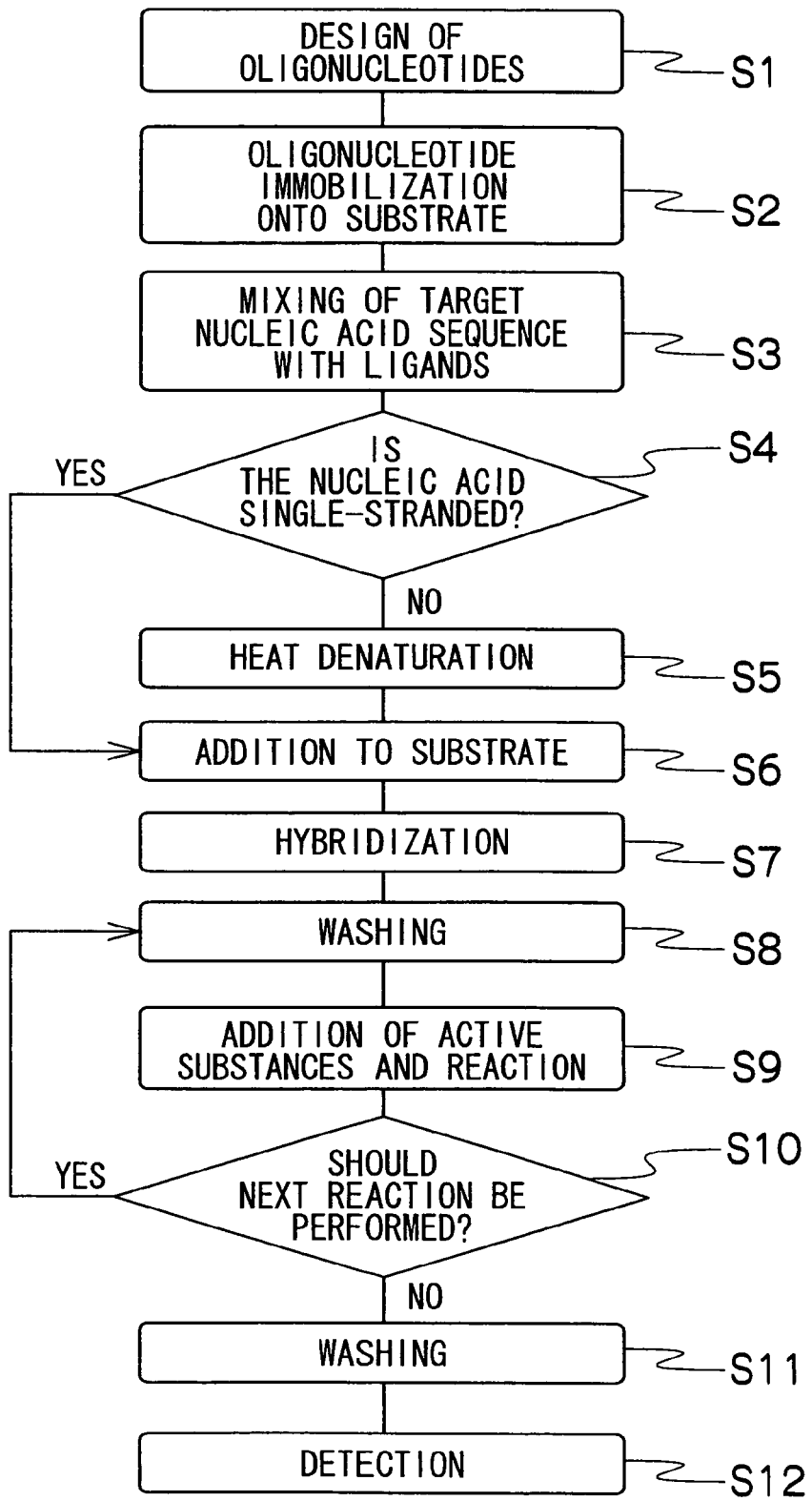
FIG. 3 is a flow chart for showing operational procedures of the first embodiment of the present invention.

Next, flows of operational procedures of performing the detection method of the first embodiment will be described with reference to the flow chart of FIG. 3 by taking, as an example, a substrate 16 having, on the surface thereof, a layer comprising a hydrophilic polymer as well as a functional group reactive to an amino group.

In a step 1, a pair of the oligonucleotide strands 12 and 14 respectively complementary to two sites in the target nucleic acid sequence 10 are designed, as described above, such that the target nucleic acid sequence 10 is cross-linked between a pair of the oligonucleotide strands 12 and 14.

Next, in a step 2, a pair of the oligonucleotide strands 12 and 14 are immobilized onto the substrate 16. For the immobilization, the oligonucleotide strands 12 and 14 are immobilized on the surface of the substrate 16 by covalently binding the oligonucleotide strands 12 and 14 through reaction to at least some of the functional groups reactive to an amino group that are present on the surface of the substrate 16 or are contained in the hydrophilic polymer. Subsequently, functional groups reactive to an amino group other than those covalently bound with the oligonucleotide strands 12 and 14 are inactivated on the surface of the substrate 16. Specifically, the oligonucleotide strands 12 and 14 can be anchored on the surface of the substrate 16 by inactivating the remaining functional groups reactive to an amino group. To remove non-immobilized oligonucleotide strands 12 and 14 on the surface of the substrate 16, the substrate 16 may be washed with pure water or a buffer solution. After washing, the functional groups reactive to an amino group other than those covalently bound with the oligonucleotide strands 12 and 14 are inactivated on the surface of the substrate 16 by treatment with an alkaline compound or with a compound having a primary amino group.

In a step 3, the sample containing the target nucleic acid sequence 10 is mixed with the ligands 22 (e.g., biotin) as a constituent of a chromogenic substance to prepare a mixture solution.

Next, in a step 4, whether the target nucleic acid sequence is single-stranded or double-stranded is determined. When the target nucleic acid sequence is double-stranded (in FIG. 3, "NO"), in a step 5, the temperature of a reaction system to which the sample has been added is increased to the melting temperature (Tm) or higher of the target nucleic acid sequence 10, for example, 90 to 95° C. The heating time is preferably approximately 1 to 10 minutes. This dissociates the double-stranded target nucleic acid sequence 10 into single strands of the target nucleic acid sequence 10. Even the single-stranded target nucleic acid sequence 10 is also heat-denatured, for example, when having a complicated secondary structure. In the step 4, when the target nucleic acid sequence is determined as being single-stranded (in FIG. 3, "YES"), the process goes to a step 6.

In the step 6, the substrate 16 and the mixture solution containing the sample and the ligands are adjusted to a hybridization temperature, and the mixture solution is added (dropwise) to the substrate. The hybridization temperature is preferably a value 2 to 8° C. lower than the melting temperatures (Tm) of the oligonucleotide strands 12 and 14.

In a step 7, hybridization reaction is performed at a temperature 2 to 8° C. lower than the melting temperatures (Tm) of the oligonucleotide strands 12 and 14. The reaction time is preferably 60 minutes or longer. This complementarily binds a pair of the oligonucleotide strands 12 and 14 thus designed to their respective complementary portions (two sites) of the target nucleic acid sequence 10 to form a cross-linked structure 18. A plurality of the cross-linked structures 18 are formed and intricately intertwined with each other to form a reticulated space 20. Then, the added ligands 22 can be captured by this reticulated space 20 through physical adsorption, thereby capturing a plurality of the ligands 22.

Next, in a step 8, the reaction solution on the substrate 16 is discarded, and the substrate 16 is washed with a washing solution, for example, a 0.1 wt % SDS solution.

Next, in a step 9, the active substances (e.g., alkaline phosphatase-labeled avidin) are added onto the substrate 16 and bound through reaction to the ligands 22 captured by the reticulated space 20. The reaction temperature and time are preferably a reaction temperature of 20 to 40° C. and a reaction time of 5 to 60 minutes.

In a next step 10, whether or not the reaction in the step 9 is further continued is determined. When the reaction is sufficient and does not have to be continued (in FIG. 3, "NO"), the process goes to a next step 11. When the reaction is insufficient and has to be continued (in FIG. 3, "YES"), the process goes back to the step 8 for the washing step. In the step 9, the active substances (e.g., BCIP/NBT) are added onto the substrate 16 and further reacted with the active substances that have already been reacted with the ligands 22 captured by the reticulated space 20. The reaction temperature and time are preferably a reaction temperature of 20 to 40° C. and a reaction time of 5 to 60 minutes.

In the step 11, the substrate 16 is washed again. In a step 12, a color signal is detected. For example, when biotin and alkaline phosphatase-labeled avidin are used as the ligands 22 and the active substances, respectively, the substrate 16 is immersed in a BCIP/NBT reagent to produce spots with a bluish-purple color. Color signals derived from the spots may be detected by visual observation or may be captured for analysis as color images into a personal computer using an image scanner. Furthermore, the degree of coloring may be measured using an absorbance detector.

As described above, when the target nucleic acid sequence 10 is present in the sample, the reticulated space 20 is formed, and a plurality of the ligands 22 as a constituent of a chromogenic substance can be held in the reticulated space 20, thereby producing a strong color signal. This achieves highly sensitive detection of the target nucleic acid sequence 10, if any, in the sample.

[Second Embodiment of the Present Invention]

FIGS. 4A to 4D are diagrams for schematically showing the mechanism of a second embodiment of a method of nucleic acid sequence detection of the present invention. A reticulated space 20 is formed by a method different from that in the first embodiment. In the description below, the same reference numerals will be used to designate the same components as those in the first embodiment.

The second embodiment of the method of nucleic acid sequence detection of the present invention mainly comprises design, immobilization, first elongation reaction, first dissociation, first cross-linking, second elongation reaction, second dissociation, second cross-linking, repetitive cross-linking, hybridization, reticulated space formation, capture, coloring, and detection steps.

The nucleic acid sequences of first and second oligonucleotide strands 24 and 26 are designed in advance such that elongation reaction products 28 and 36 produced through elongation reaction respectively form a cross-linked structure in the relationship of nucleic acid sequences among a target nucleic acid sequence 19 and the first and second oligonucleotide strands 24 and 26 (design step). Specifically, the first and second oligonucleotide strands 24 and 26 are designed such that the first elongation reaction product 28 in a first duplex 30 formed through first elongation reaction using the first oligonucleotide strand 24 as a primer and the target nucleic acid sequence 19 as a template after complementary binding of the target nucleic acid sequence 19 and the first oligonucleotide strand 24 can be dissociated from the target nucleic acid sequence 19 and bind to the second oligonucleotide strand 26 having a complementary nucleic acid sequence thereto. Information about the nucleic acid sequence of the target nucleic acid sequence 19 can be obtained from DNA data banks, as in the first embodiment.

Figure 4A:
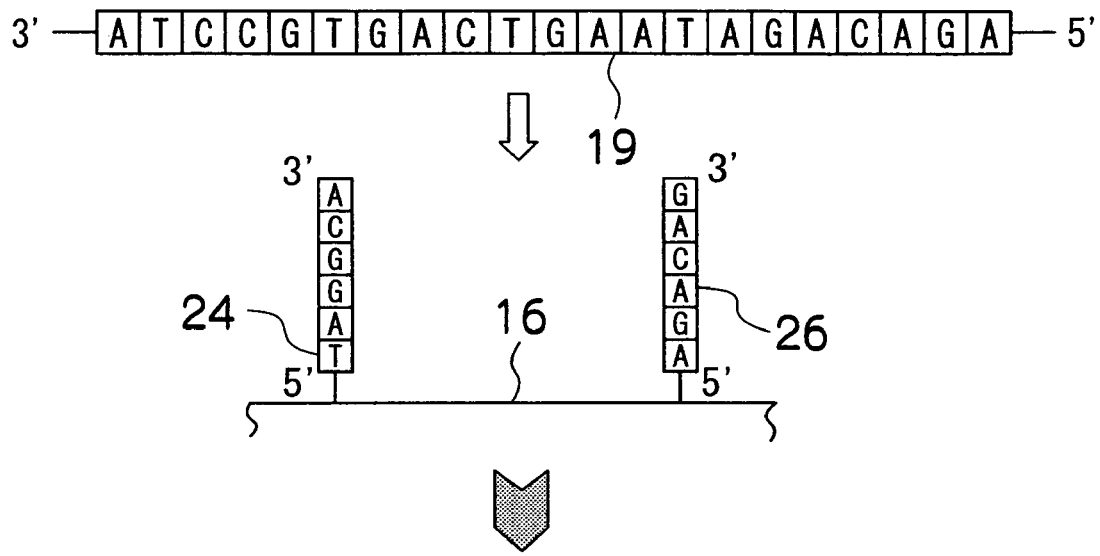
FIGS. 4A to 4D are diagrams for schematically showing the mechanism of a second embodiment of a method of nucleic acid sequence detection of the present invention using the target nucleic acid sequence 19 (SEQ ID NO:6) to produce the first elongation reaction product 28 (SEQ ID NO:7)
Figure 4B:
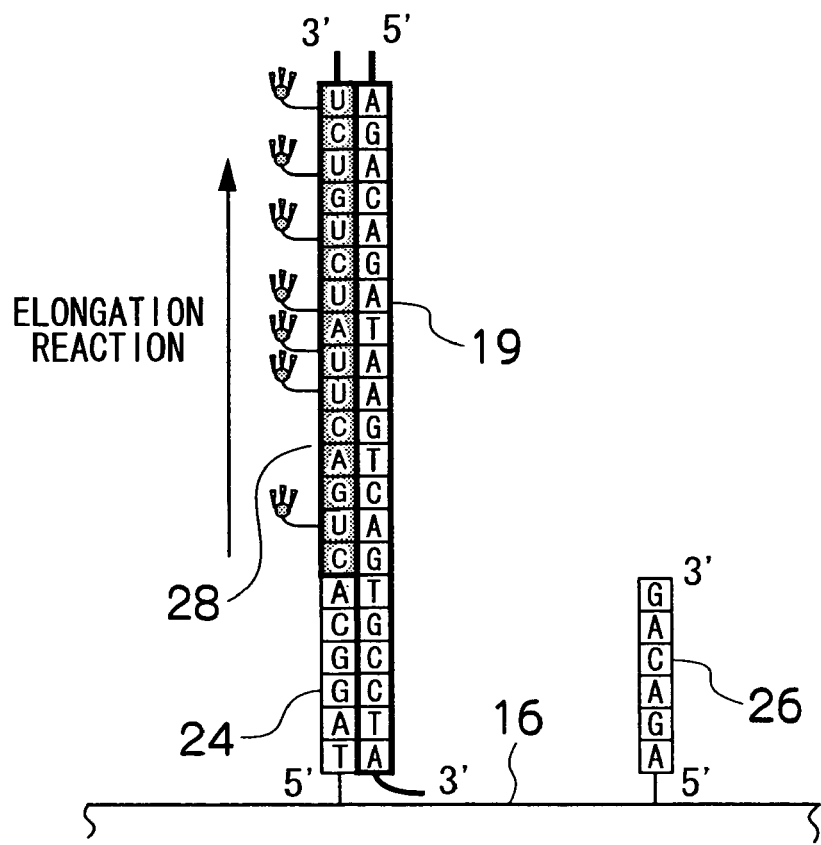

The first oligonucleotide strand 24 shown on the left side in FIG. 4A has a nucleic acid sequence 5'-TAGGCA-3' (SEQ ID NO:21) starting from the substrate 16 side, which is designed to be complementary to a sequence portion 3'-ATCCGT-5' (SEQ ID NO:3) at one end of the target nucleic acid sequence 19. Alternatively, the second oligonucleotide strand 26 shown on the right side in FIG. 4A has a nucleic acid sequence 5'-AGACAG-3' (SEQ ID NO:22) starting from the substrate 16 side, which is designed to be complementary to a sequence portion 3'-UCUGUC-5' (SEQ ID NO:8) at one end of the first elongation reaction product 28. In this context, the base U (uracil) used in elongation reaction is biotinylated in the diagrams. A base T is used for non-biotinylation. The base U originally constitutes RNA. However, biotinylated U is analogous to the base T in terms of chemical structures and can therefore be used in elongation reaction catalyzed by DNA polymerase.

Next, as shown in FIG. 4A, a pair of the oligonucleotide strands 24 and 26 are anchored onto the substrate 16 by immobilizing the 5'-ends of the first and second oligonucleotide strands 24 and 26 onto the substrate 16 (immobilization step).

FIG. 4A shows only each one of the first and second oligonucleotide strands 24 and 26. In actuality, a plurality of the first and second oligonucleotide strands 24 and 26 are anchored on the substrate 16.

The sample containing the target nucleic acid sequence 19 is spotted (added dropwise) onto the substrate 16 thus prepared to perform the first elongation reaction to detection steps. Specifically, the first oligonucleotide strand 24 binds to its complementary portion of the target nucleic acid sequence 19 dissociated into single strands through heat denaturation. Then, elongation reaction is performed using the target nucleic acid sequence 19 as a template and the first oligonucleotide strand 24 as a primer to form a double-stranded nucleic acid sequence shown in FIG. 4B, as in the conventional MPEX method (first elongation reaction step). However, when the elongation reaction is performed in the temperature region of Tm (melting temperature) of the first and second oligonucleotide strands 24 and 26, the complementary regions in the elongation reaction product 28 to the oligonucleotide strands 24 and 26 may be dissociated into single strands at any time. Moreover, the second oligonucleotide strand 26 designed in advance such that it complementarily binds to the elongation reaction product 28 is immobilized on the substrate 16. Therefore, a portion of the elongation reaction product 28 is dissociated from the target nucleic acid sequence 19 (first dissociation step) and then binds to the second oligonucleotide strand 26 to form a cross-linked state (first cross-linking step).

Figure 4C:
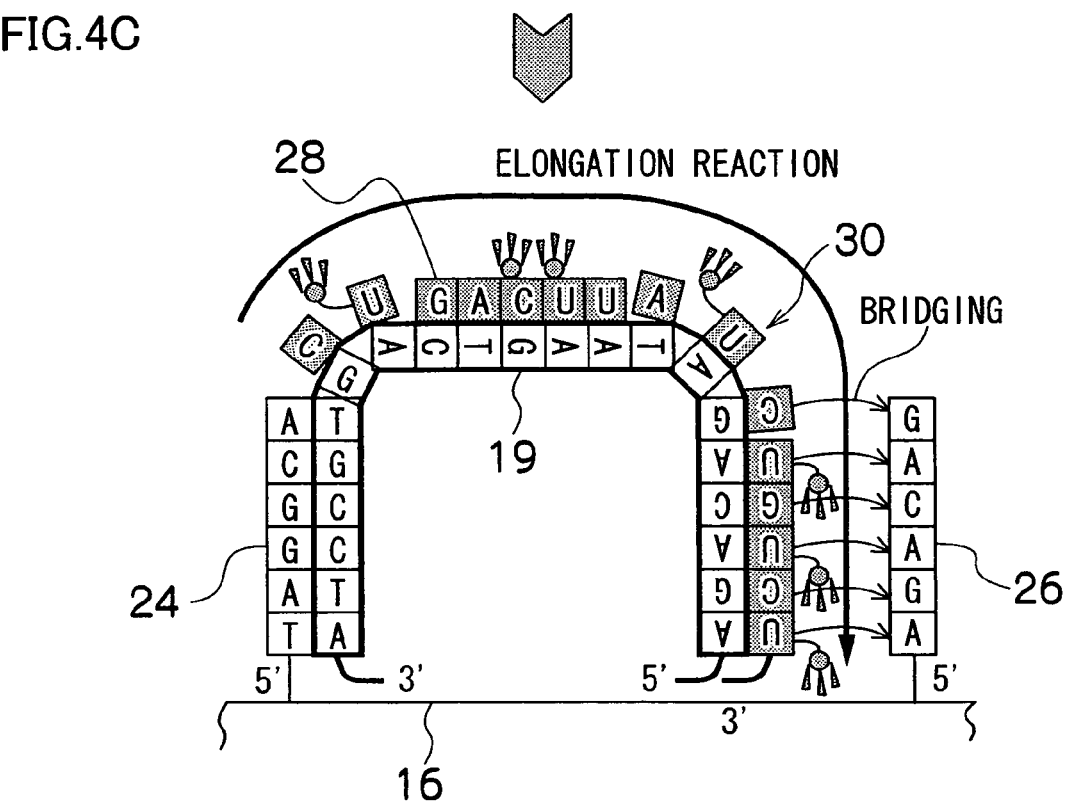

Specifically, the complementary regions in the first elongation reaction product 28 extended through the first elongation reaction to the oligonucleotide strands 24 and 26 seek to take a stable state in terms of molecular structures under unstable energy conditions of the Tm temperature region. Therefore, as shown in FIG. 4C, the first elongation reaction product 28 binds to the second oligonucleotide strand 26 having a complementary sequence thereto. The term "Bridging" described in FIG. 4C means that the target nucleic acid sequence is cross-linked between two or more oligonucleotides anchored by one end. In such a sense, the cross-link of the target nucleic acid sequence 10 with a pair of the oligonucleotide strands 12 and 14 in the first embodiment is also included in bridging.

In this context, nucleic acid sequences other than the target nucleic acid sequence 19 contained in the sample neither have a complementary relationship with the first oligonucleotide strand 24 nor bind to the first oligonucleotide strand 24 for elongation reaction.

An enzyme used in the first elongation reaction includes DNA polymerase, RNA polymerase, and a mixture thereof.

Figure 4D:
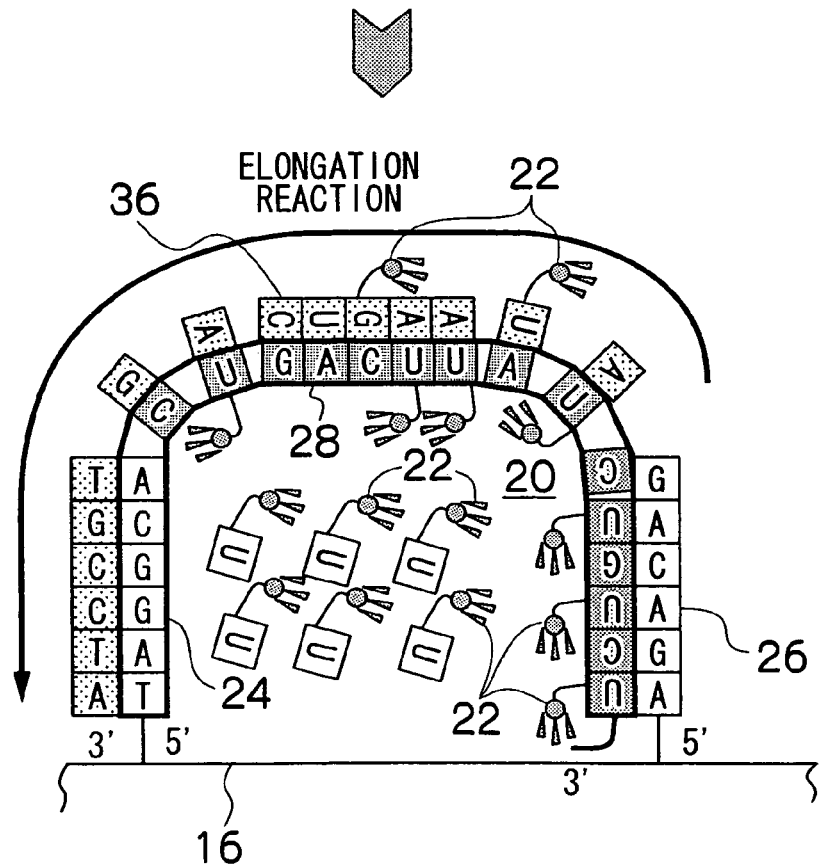

Next, elongation reaction shown in FIG. 4D occurs using the second oligonucleotide strand 26 as a primer and the first elongation reaction product 28 as a template (second elongation reaction step). For the sake of simplification, the target nucleic acid sequence 19 is not shown in FIG. 4D. In actuality, the target nucleic acid sequence 19 is dissociated from the first oligonucleotide strand 24 and binds to a different first oligonucleotide strand.

An enzyme used in the second or later elongation reaction is DNA polymerase. This DNA polymerase may be pol I (e.g., Taq (Takara-Bio Inc.)) DNA polymerase and is preferably thermostable α-DNA polymerase (e.g., KOD (TOYOBO CO., LTD.)), more preferably DNA polymerase having strand displacement activity. The DNA polymerase having strand displacement activity easily cleaves hydrogen bonds in a double-stranded portion, if any, in template DNA or cDNA to continue elongation reaction. Examples of the DNA polymerase having strand displacement activity include Klenow Fragment, phi29 DNA polymerase, BcaBEST DNA polymerase, and Bst DNA polymerase. The reaction temperature is preferably the Tm values or higher of the first and second oligonucleotide strands 24 and 26 and lower than 65° C. The reaction time is preferably 20 to 90 minutes.

A plurality of the first and second oligonucleotide strands 24 and 26 are immobilized on the substrate 16. Thus, the second elongation reaction product 36 extended in the second elongation reaction step is dissociated from the first elongation reaction product 28 (second dissociation step) and binds to a first oligonucleotide strand 24 different from the first oligonucleotide strand 24 but with the same nucleic acid sequence to form a cross-linked state (second cross-linking step). In this state, the first oligonucleotide strand 24 serves as a primer. Therefore, the first and second cross-linking steps are repeated between the first and second oligonucleotide strands 24 and 26 (repetitive cross-linking step). Then, the temperature is set to a hybridization temperature for the oligonucleotide strands (hybridization step) to form a larger number of cross-linked structures on the substrate 16. The hybridization temperature is preferably a temperature 2 to 8° C. lower than the melting temperatures (Tm) of the oligonucleotide strands 24 and 26.

Figure 5:
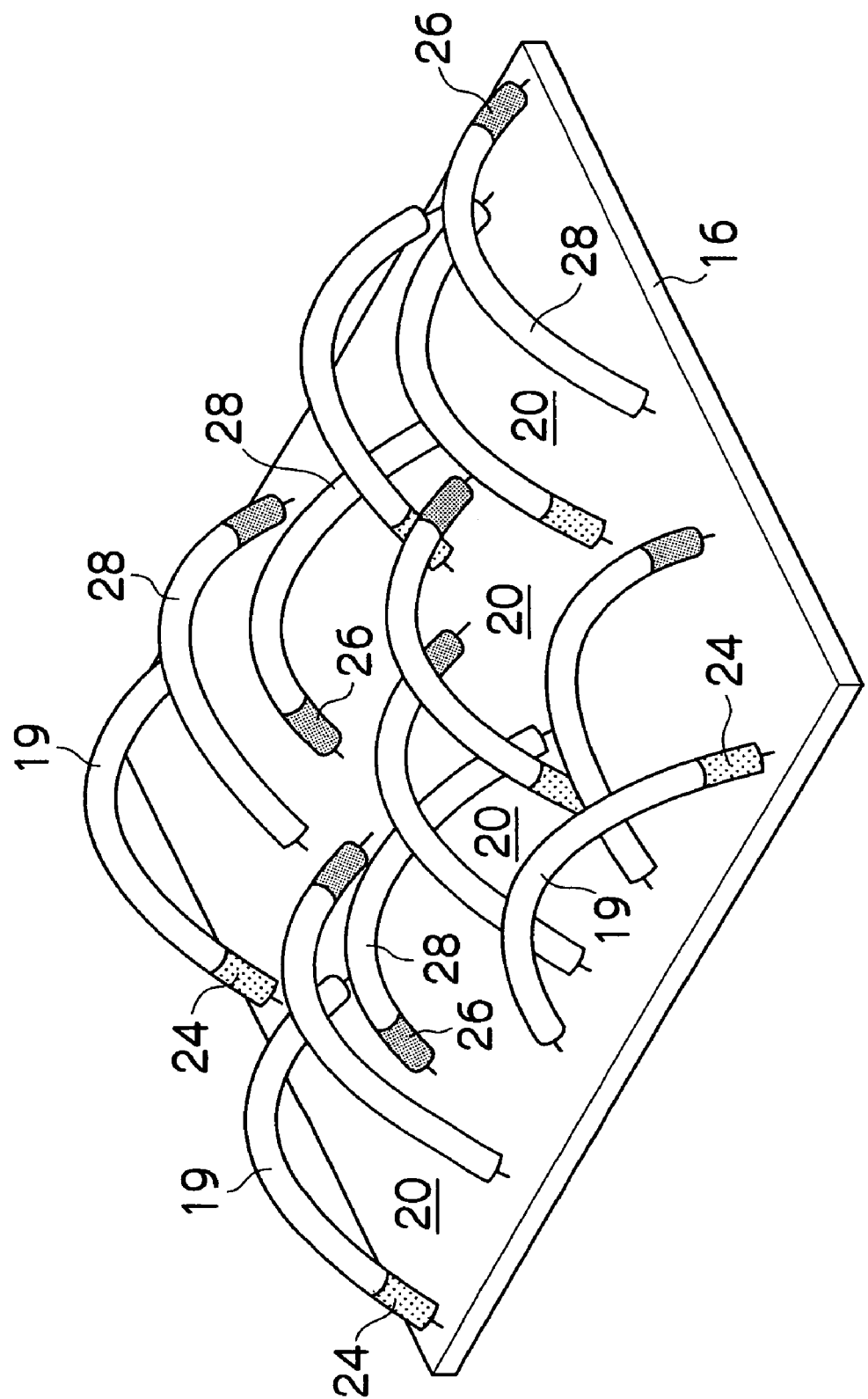
FIG. 5 is a diagram for schematically showing a reticulated space formed in the second embodiment of the present invention.

As shown in FIG. 5, this forms a finely reticulated space 20 wherein a plurality of the cross-linked structures are intertwined with each other (reticulated space formation step). As in the first embodiment, a plurality of ligands 22 are captured by the reticulated space 20 (capture step) and caused to color with active substances reactive to the ligands 22 (coloring step). Highly sensitive detection can be performed by detecting a color signal derived from the coloring.

(Operational Procedures of Performing Detection Method of Second Embodiment)

Figure 6:
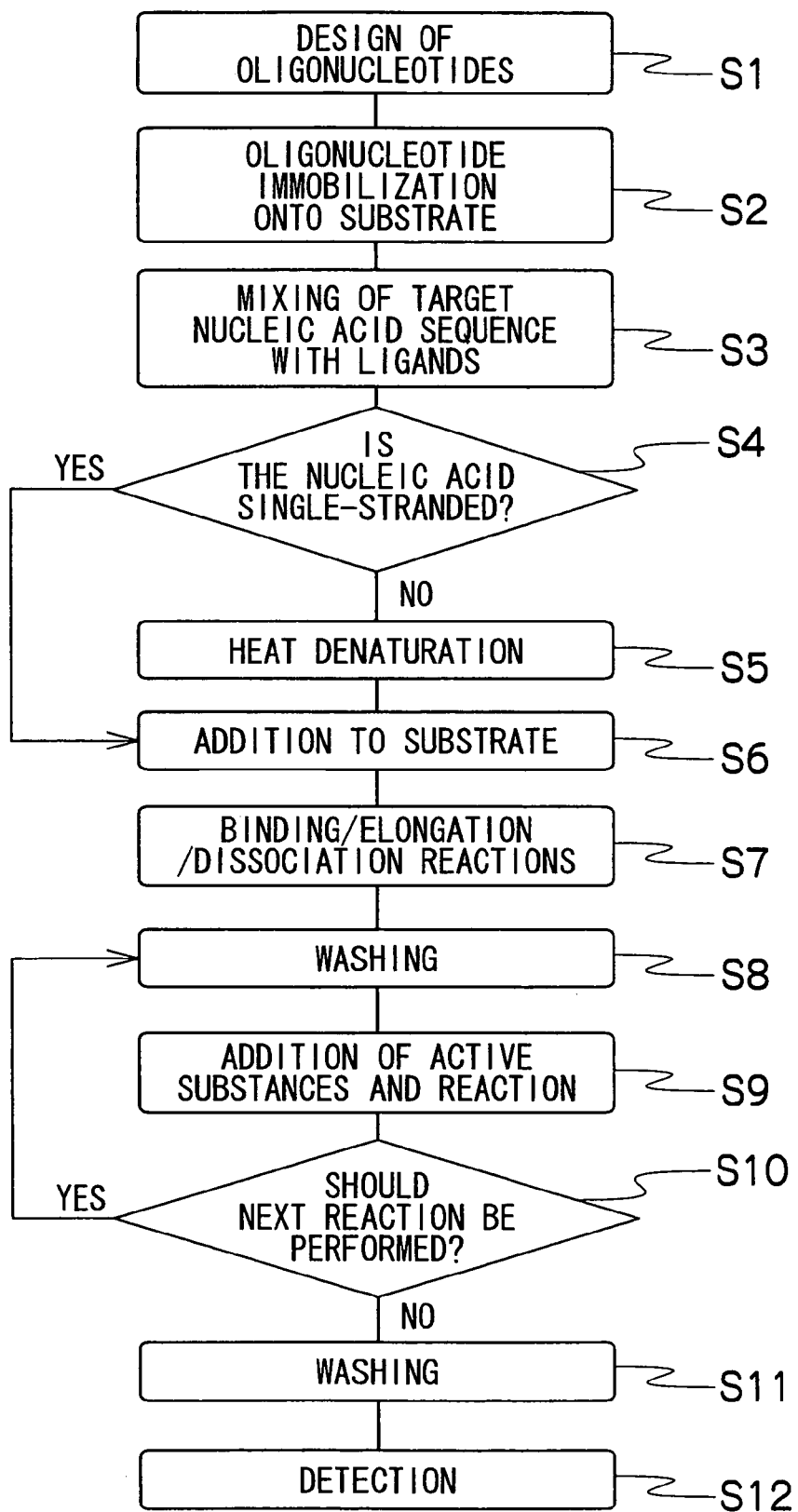
FIG. 6 is a flow chart for showing operational procedures of the second embodiment of the present invention.

Next, flows of operational procedures of performing the detection method of the second embodiment will be described with reference to the flow chart of FIG. 6 by taking, as an example, a substrate 16 having, on the surface thereof, a layer comprising a hydrophilic polymer as well as a functional group reactive to an amino group.

In a step 1, the nucleic acid sequences of the first and second oligonucleotide strands 24 and 26 are designed, as described above, such that elongation reaction products 28 and 36 produced through elongation reaction respectively form a cross-linked structure in the relationship of nucleic acid sequences among the target nucleic acid sequence 19 and the first and second oligonucleotide strands 24 and 26.

In a step 2, the designed first and second oligonucleotide strands 24 and 26 are immobilized onto the substrate 16. The immobilization is performed in the same way as in the first embodiment, and the description thereof is omitted.

In a step 3, the sample containing the target nucleic acid sequence 19 is mixed with the ligands 22 (e.g., biotinylated dUTP) as a constituent of a chromogenic substance to prepare a mixture solution.

Next, in a step 4, whether the target nucleic acid sequence is single-stranded or double-stranded is determined. When the target nucleic acid sequence is double-stranded (in FIG. 6, "NO"), in a step 5, the temperature of a reaction system to which the sample has been added is increased to the melting temperature (Tm) or higher of the target nucleic acid sequence 19, for example, 90 to 95° C. The heating time is preferably approximately 1 to 10 minutes. This dissociates the double-stranded target nucleic acid sequence 19 into single strands of the target nucleic acid sequence 19. Even the single-stranded target nucleic acid sequence 19 is also heat-denatured, for example, when having a complicated secondary structure. In the step 4, when the target nucleic acid sequence is determined as being single-stranded (in FIG. 6, "YES"), the process goes to a step 6.

In the step 6, the mixture solution containing the sample and the ligands are added (dropwise) to the substrate.

Next, in a step 7, the first elongation reaction, first dissociation, first cross-linking, second elongation reaction, second dissociation, second cross-linking, repetitive cross-linking, hybridization, reticulated space formation, and capture steps are performed.

Specifically, in the first elongation reaction step, elongation reaction is performed using the target nucleic acid sequence 19 as a template and the first oligonucleotide strand 24 as a primer. In the first dissociation step, the elongation reaction product 28 is dissociated from the target nucleic acid sequence 19. In the first cross-linking step, the dissociated elongation reaction product 28 is bound to the second oligonucleotide strand 26 to form a cross-linked state.

Next, in the second elongation reaction step, elongation reaction is performed using the second oligonucleotide strand 26 as a primer and the first elongation reaction product 28 as a template. In the second dissociation step, the second elongation reaction product 36 extended in the second elongation reaction step is dissociated from the first elongation reaction product 28. In the second cross-linking step, the dissociated second elongation reaction product 36 is bound to a first oligonucleotide strand 24 different from the first oligonucleotide strand 24 but with the same nucleic acid sequence to form a cross-linked state.

Then, in the repetitive cross-linking step, the first and second cross-linking steps are repeated between the first and second oligonucleotide strands 24 and 26. Then, in the hybridization step, the temperature is set to a hybridization temperature for the oligonucleotide strands to form a larger number of cross-linked structures on the substrate 16. This forms a finely reticulated space 20 on the substrate 16, wherein a plurality of the cross-linked structures are intertwined with each other (reticulated space formation step).

After formation of the reticulated space 20, the steps 8 to 12 can be performed in the same way as in the first embodiment, thereby highly sensitively detecting the target nucleic acid sequence 19.

As described above, the mixture solution containing the target nucleic acid sequence 19 and the ligands 22 is prepared in the step 3. Alternatively, the ligands 22 may be added at some time between the steps 6 and 7.

[Modification of Second Embodiment of the Present Invention]

Two oligonucleotide strands, the first and second oligonucleotide strands 24 and 26, are used in the second embodiment of the present invention described above. Alternatively, three or more oligonucleotide strands can also be used.

The modification of the second embodiment will be described by taking three oligonucleotide strands as an example. The second elongation reaction product 36 dissociated in the second dissociation step of the second embodiment binds to a third oligonucleotide strand designed such that it has a complementary nucleic acid sequence to the second elongation reaction product 36. After binding, elongation reaction is performed in the same way, and the elongation reaction product is dissociated therefrom and binds to a first oligonucleotide strand to form a cross-linked structure on the substrate 16. A repetitive cross-linking step is performed on these first to third oligonucleotide strands to form a finely reticulated space.

Thus, the second embodiment of the present invention can also be applied to three or more oligonucleotide strands by designing in advance oligonucleotide strands complementary to elongation reaction products dissociated one after another.

Preferably, the substrate 16 used in the second embodiment has, on the surface thereof, a layer comprising a hydrophilic polymer as well as a functional group reactive to an amino group. This binds an elongation reaction product dissociated through heat denaturation from a duplex formed through elongation reaction, to a different oligonucleotide strand for additional elongation reaction.

[Nucleic Acid Sequence Detection Substrate]

In the first and second embodiments, oligonucleotide strands are immobilized onto a substrate to prepare a nucleic acid sequence detection substrate. For example, the presence of a particular target nucleic acid sequence to be detected in a sample can be detected highly sensitively only by spotting (adding) the sample containing the target nucleic acid sequence onto this nucleic acid sequence detection substrate.

EXAMPLES

Example 1

Next, a detection method of a first embodiment of the present invention will be described with reference to Example. A target nucleic acid sequence used was a nucleic acid sequence specific to norovirus. The detection method of the first embodiment will be described by taking the detection of this target nucleic acid sequence as an example.

Specifically, according to an approach described below, a pair of oligonucleotide strands complementary to the target nucleic acid sequence were immobilized onto the surface of a plastic substrate, to which the target nucleic acid sequence as a sample was in turn added and bound to a pair of the oligonucleotide strands on the substrate to form a structure in which the nucleic acid sequence was cross-linked therewith. A finely reticulated space was formed based on the structure. Then, ligands as a constituent of a chromogenic substance could be captured in a large amount by the reticulated space through physical adsorption. This achieved highly sensitive detection of the target nucleic acid sequence.

Specifically, a PCR product of norovirus cDNA was used as the target nucleic acid sequence for experiments. This PCR product was obtained by PCR targeted for a region ORF2 encoding a capsid protein, a norovirus structural protein. Since norovirus is divided into two groups, G1 and G2, two PCR products derived from G1 and G2 were prepared for experiments.

(Preparation of Target Nucleic Acid Sequence)

Feces were dissolved in a phosphate buffer solution to prepare a 10% emulsion. After cooling centrifugation at 12,000 rpm, RNA was extracted from the centrifugation supernatant. The centrifugation supernatant was warmed to room temperature, and RNA was extracted and purified therefrom using an RNA extraction/purification kit (QIAamp Viral RNA Mini Kit (QIAGEN)). Then, to 24 µL, of the RNA extracts, 3 µL of a 5-fold concentrated RT-PCR buffer, 1 µL of sterilized water, and 2 µL of DNase (DNase I (Takara Bio Inc.); 1 U/µL) were added, and the mixture was reacted at 37° C. for 30 minutes and at 75° C. for 5 minutes and then cooled on ice. The obtained RNA was reverse-transcribed (42° C. for 1 hour (1 cycle), 99° C. for 5 minutes (1 cycle), and 4° C.) into cDNA using random primers (Random Primer Hexamer (Amersham Pharmacia)) and an RT reaction kit (SuperScript II Reverse Transcriptase RNase H-Reverse Transcriptase (Invitrogen)). PCR reaction (94° C. for 3 minutes (1 cycle); 94° C. for 1 minute, 50° C. for 1 minute, and 72° C. for 2 minutes (40 cycles); and 72° C. for 15 minutes (1 cycle)) was performed using this cDNA as a template, primers 1 (25 µM), 2 (25 µM), 3 (25 µM), and 4 (25 µM), and DNA polymerase (ExTaq (Takara Bio Inc.)) to separately prepare G1 and G2 PCR products, which were in turn electrophoresed for the confirmation of amplification, then purified, and used as target nucleic acid sequences.

(Plastic Substrate Used)

Figures 7A, 7B, 7C:
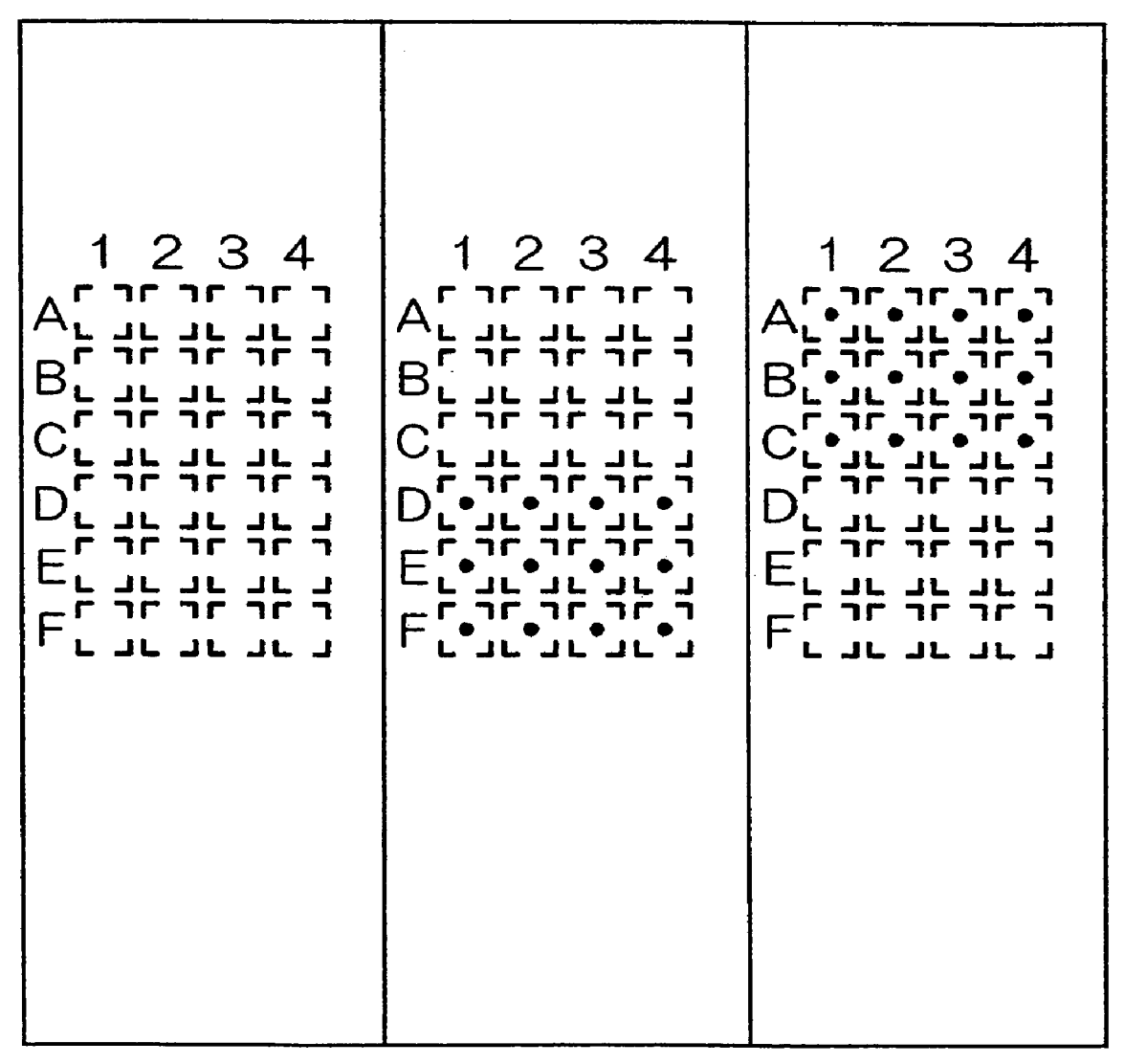

A commercially available plastic DNA array substrate (S-BIO® PrimeSurface® manufactured by SUMITOMO BAKELITE Co., Ltd.) was used in experiments. This substrate is a plastic substrate having, on the surface thereof, a layer comprising a hydrophilic polymer as well as a functional group reactive to an amino group, which is described in the embodiments. As shown in FIGS. 7A to 7C, the substrate has a total of 24 spot regions including 4 columns (1 to 4)×6 rows (A to F). The presence or absence of each nucleic acid sequence was evaluated in each spot region. In the present experiment, the plastic substrate was prepared such that 12 spot regions and 12 spot regions were used for the detection of G1 and G2 PCR products, respectively.

(Immobilization of Oligonucleotide Strands)

For the detection of the G1 PCR product, a pair of oligonucleotide strands 1 and 2 comprising nucleic acid sequences shown below were synthesized. The oligonucleotide strands 1 and 2 respectively had a complementary sequence to the G1 PCR product. The oligonucleotide strand 1 is a 20-base nucleotide strand modified at the 5'-end with an amino group. This oligonucleotide strand 1 was dissolved in a 0.25 M carbonate buffer (pH 9.0) to prepare a 1 µM oligonucleotide solution.

On the other hand, the oligonucleotide strand 2 is a 20-base nucleotide strand modified at the 3'-end with an amino group. This oligonucleotide strand 2 was dissolved in a 0.25 M carbonate buffer (pH 9.0) to prepare a 1 µM oligonucleotide solution.

Then, the solution of the oligonucleotide strand 1 was mixed with the solution of the oligonucleotide strand 2, and the mixture was spotted onto the surface of each plastic substrate using a spotter (Marks-I manufactured by Hitachi Software Engineering Co., Ltd.) and a cross cut pin of 100 µm in diameter. Specifically, the solution was spotted onto 12 spot regions (spot regions 1 to 12) including columns 1 to 4×rows A to C in the plastic substrate shown in FIG. 7C. Then, each substrate comprising the oligonucleotide strands spotted thereon was heated at 80° C. for 1 hour to immobilize each oligonucleotide strand thereonto.

For the detection of the G2 PCR product, oligonucleotide strands 3 and 4 comprising nucleic acid sequences shown below were synthesized. The oligonucleotide strands 3 and 4 respectively had a complementary sequence to the G2 PCR product. The oligonucleotide strand 3 is a 20-base nucleotide strand modified at the 5'-end with an amino group. This oligonucleotide strand 3 was dissolved in a 0.25 M carbonate buffer (pH 9.0) to prepare a 1 µM oligonucleotide solution.

On the other hand, the oligonucleotide strand 4 is a 23-base nucleotide strand modified at the 3'-end with an amino group. This oligonucleotide strand 4 was dissolved in a 0.25 M carbonate buffer (pH 9.0) to prepare a 1 µM oligonucleotide solution.

Then, the solution of the oligonucleotide strand 3 was mixed with the solution of the oligonucleotide strand 4, and the mixture was spotted onto the surface of each plastic substrate using a spotter (Marks-I manufactured by Hitachi Software Engineering Co., Ltd.) and a cross cut pin of 100 µm in diameter. Specifically, the solution was spotted onto 12 spot regions (spot regions 13 to 24) including columns 1 to 4×rows D to F in the plastic substrate shown in FIG. 7B. Then, each substrate comprising the oligonucleotide strands spotted thereon was heated at 80° C. for 1 hour to immobilize each oligonucleotide strand thereonto.

The nucleic acid sequences of the primers 1 to 4 used for preparing the G1 and G2 PCR products as well as the nucleic acid sequences of the oligonucleotide strands 1 to 4 immobilized on the plastic substrates are shown below.

```
Primer 1 (COG1F):
                                      (SEQ ID NO: 9)
5'-CGYTGGATGCGNTTYCATGA-3'

Primer 2 (G1-SKR):
                                      (SEQ ID NO: 10)
5'-CCAACCCARCCATTRTACA-3'
```

```
Primer 3 (COG2F):
                                      (SEQ ID NO: 11)
5'-CARGARBCNATGTTYAGRTGGATGAG-3'

Primer 4 (G2-SKR):
                                      (SEQ ID NO: 12)
5'-CCRCCNGCATRHCCRTTRTACAT-3'

Oligonucleotide Strand 1 (G1SKF):
                                      (SEQ ID NO: 13)
5'-CTGCCCGAATTYGTAAATGA-3'

Oligonucleotide Strand 2 (G1-1'):
                                      (SEQ ID NO: 14)
5'-CCAACAAACATGGATGGCAC-3'

Oligonucleotide Strand 3 (RING2AL-TP):
                                      (SEQ ID NO: 15)
5'-TGGGAGGGSGATCGCRATCT-3'

Oligonucleotide Strand 4 (G2SKRrc):
                                      (SEQ ID NO: 16)
5'-ATGTAYAAYGGDYATGCNGGYGG-3'

IUB Codes (Code of international Union of
Biochemistry). R = A or G; B = C, G or T;
Y = C or T; D = A, G or T; K = G or T;
H = A, C or T; M = A. or C; V = A, C or G;
S = G or C; W = A or T; N = any base.
```

(Hybridization)

59 µL of the prepared target nucleic acid sequence, 13 µL of a hybridization buffer, and 8 µL of biotin were mixed to prepare a mixture solution, which was in turn added to the plastic substrate comprising the pairs of the oligonucleotide strands (a pair of the oligonucleotide strands 1 and 2 and a pair of the oligonucleotide strands 3 and 4) thus immobilized thereon.

The substrate shown in FIG. 7A denotes that a target nucleic acid sequence-free sample was added to the substrate comprising the oligonucleotide strands thus immobilized thereon.

A reaction system on each substrate was then heated under conditions involving 95° C. for 8 minutes, thereby dissociating the double-stranded target nucleic acid sequence into single strands through heat denaturation. The reaction system was further subjected to hybridization at 54° C. for 90 minutes.

Next, after washing, 0.01 mg/mL alkaline phosphatase-labeled streptavidin was added onto the substrate. The substrate was covered with cover glass, and the reaction system was reacted at 37° C. for 30 minutes. Then, the substrate was washed and immersed in a BCIP/NBT (BCIP/NBT Phosphatase Substrate (1-Component System) (KPL)) coloring reagent. The reaction system was reacted at 37° C. for 30 minutes, and the substrate was washed to produce spots with a bluish-purple color. Color signals were captured as color images into a personal computer using an image scanner (PIXUS MP470 manufactured by Canon Inc.). Color intensity was digitized using image analysis software (Daredemo DNA Array analysis software manufactured by SUMITOMO BAKELITE Co., Ltd.). The color images are shown in FIGS. 7A to 7C. Moreover, an average S/N ratio (Signal to Noise Ratio) of the digitization results was determined according to the formula I below and is shown in Table 1 of FIG. 8.

$$S/N \text{ ratio} = 1 \times S/(S+N) \qquad \text{Formula 1}$$

S/N: ratio of measured color intensity to intensity of background noise: 1.0 at the maximum
S: measured color signal intensity
N: intensity of background noise As a result, when the G1 PCR product was used as a target nucleic acid sequence, only the spot regions 1 to 12 produced a color, as can be seen from FIG. 7C. On the other hand, when the G2 PCR product was used as a target nucleic acid sequence, only the spot regions 13 to 24 produced a color, as can be seen from FIG. 7B.

When the PCR product (target nucleic acid sequence)-free sample was used as a control, neither the immobilization of the oligonucleotide strands 1 and 2 nor the immobilization of the oligonucleotide strands 3 and 4 produced a color, as can be seen from FIG. 7A.

Eighteen plastic DNA array substrates were prepared (not shown), each of which comprised spots comprising only the oligonucleotide strand 1 (spot regions 1 to 6) and only the oligonucleotide strand 2 (spot regions 7 to 12) immobilized thereon for the detection of the G1 PCR product as well as spots comprising only the oligonucleotide strand 3 (spot regions 13 to 18) and only the oligonucleotide strand 4 (spot regions 19 to 24) immobilized thereon for the detection of the G2 PCR product. Then, the G1 and G2 PCR products were hybridized to 6 substrates each by the method described above. At the same time, biotin was added onto each substrate. After washing, alkaline phosphatase-labeled avidin was added onto the substrate. The substrate was covered with cover glass and left at 37° C. for 30 minutes. Then, the substrate was washed and immersed in a BCIP/NBT coloring reagent. The reaction system was reacted at 37° C. for 30 minutes, and the substrate was washed to produce spots with a bluish-purple color.

Color signals were captured as color images into a personal computer using an image scanner (PIXUS MP470 manufactured by Canon Inc.). Color intensity was digitized using image analysis software (Daredemo DNA Array analysis software manufactured by SUMITOMO BAKELITE Co., Ltd.).

As a result, all of the spot regions 1 to 24 were confirmed to produce no color. The PCR product-free 6 plastic DNA array substrates as a control also produced no color.

The S/N ratio of an average value of the color signal intensities (S) of the G1 PCR product shown in the spot regions 1 to 12 in FIG. 7C to an average value of background noise intensities (N) in FIG. 7A was 0.97, as can be seen from Table 1 of FIG. 8. Thus, exceedingly highly sensitive detection was achieved.

Likewise, the S/N ratio of an average value of the color signal intensities (S) of the G2 PCR product shown in the spot regions 13 to 24 in FIG. 7B to an average value of background noise intensities (N) in FIG. 7A was 0.98. Thus, exceedingly highly sensitive detection was achieved.

Example 2

Next, a detection method of a second embodiment of the present invention will be described with reference to Example. A nucleic acid sequence specific to norovirus was used as a target nucleic acid sequence, as in Example 1. The detection method of the second embodiment will be described by taking the detection of this target nucleic acid sequence as an example.

Specifically, according to an approach described below, a first oligonucleotide strand immobilized on the surface of a substrate complementarily binds to the target nucleic acid sequence. Then, elongation reaction is performed using the first oligonucleotide strand as a primer and the target nucleic acid sequence as a template. The elongation reaction product having a complementary sequence to the target nucleic acid sequence is dissociated therefrom through dissociation reaction.

Then, the dissociated first elongation reaction product complementarily binds to a second oligonucleotide strand also immobilized on the surface of the substrate. Then, elongation reaction is performed using the second oligonucleotide strand as a primer and the first elongation reaction product as a template. The elongation reaction product having a complementary sequence to the first elongation reaction product is dissociated therefrom through dissociation reaction.

A finely reticulated space was formed on the substrate by repeating these procedures. Ligands were captured by the reticulated space through physical adsorption. The target nucleic acid sequence was detected by using active substances reactive to the ligands.

(Preparation of Target Nucleic Acid Sequence)

The G1 and G2 PCR products of norovirus cDNA shown in Example 1 were separately prepared and purified. Then, their concentrations were adjusted to 0, $10^0$, $10^1$, $10^2$, $10^4$, $10^6$, and $10^8$ copies/μL, and the G1 and G2 PCR products were used as target nucleic acid sequences in experiments. Evaluation was conducted using a sample supplemented with sterilized water as a background.

(Plastic Substrate)

Each oligonucleotide strand was anchored by one end on the surface of an MPEX (Multiple Primer EXtension)-compatible substrate of the plastic substrate (S-BIO® PrimeSurface® manufactured by SUMITOMO BAKELITE Co., Ltd.) shown in Example 1, and the prepared substrate was used in experiments.

The MPEX method (K. Kinoshita et al., Multiple primer extension by DNA polymerase on a novel plastic DNA array coated with a biocompatible polymer, Nucleic Acid Research, Vol. 35, No. 1, 2007, pp. e3, and Japanese Patent Application Laid-Open Nos. 2006-174788 and 2007-222010) is described in the Description of the Related Art. For a control in the present Example 2, the target nucleic acid sequence was detected by the MPEX method using only one kind of oligonucleotide strand immobilized on the substrate, wherein an elongation reaction product does not form a cross-linked structure. Evaluation was conducted using a sample supplemented with sterilized water as a background.

(Immobilization of Oligonucleotide Strands)

In Example 2, for the detection of the G1 PCR product, oligonucleotide strands 5 and 6 shown below were synthesized. The oligonucleotide strand 5 had a complementary sequence to the G1 PCR product. The oligonucleotide strand 5 is a 20-base nucleotide strand modified at the 5'-end with an amino group. This oligonucleotide strand 5 was dissolved in a 0.25 M carbonate buffer (pH 9.0) to prepare a 1 μM oligonucleotide solution.

On the other hand, the oligonucleotide strand 6 is a 19-base nucleotide strand also modified at the 5'-end with an amino group. This oligonucleotide strand 6 was dissolved in a 0.25 M carbonate buffer (pH 9.0) to prepare a 1 μM oligonucleotide solution.

In Example 2, these solutions of the oligonucleotide strands 5 and 6 were mixed, and the mixture was spotted onto the surface of each plastic substrate (spot regions 1 to 4) using a spotter (Marks-I manufactured by Hitachi Software Engineering Co., Ltd.) and a cross cut pin of 100 μm in diameter. The substrates (not shown) used in Example 2 were prepared in a similar way as in those shown in FIGS. 7A to 7C.

On the other hand, only one of the oligonucleotide strands 5 and 6 was spotted (1 µM) onto spot regions on the substrates (spot regions 5 to 8 and 9 to 12, respectively) for the control experiment.

Then, each of the substrates of Example 2 and the control substrate was heated at 80° C. for 1 hour to immobilize each oligonucleotide strand thereonto.

In Example 2, for the detection of the G2 PCR product, oligonucleotide strands 7 and 8 were synthesized. The oligonucleotide strand 7 had a complementary sequence to the G2 PCR product. The oligonucleotide strand 7 is a 26-base nucleotide strand modified at the 5'-end with an amino group. This oligonucleotide strand 7 was dissolved in a 0.25 M carbonate buffer (pH 9.0) to prepare a 1 µM oligonucleotide solution.

On the other hand, the oligonucleotide strand 8 is a 20-base nucleotide strand also modified at the 5'-end with an amino group. This oligonucleotide strand 8 was dissolved in a 0.25 M carbonate buffer (pH 9.0) to prepare a 1 µM oligonucleotide solution.

In Example 2, these solutions of the oligonucleotide strands 7 and 8 were mixed, and the mixture was spotted onto the surface of each plastic substrate (spot regions 13 to 16) using a spotter (Marks-I manufactured by Hitachi Software Engineering Co., Ltd.) and a cross cut pin of 100 µm in diameter.

On the other hand, only one of the oligonucleotide strands 7 and 8 was spotted (1 µM) onto spot regions on the substrates (spot regions 17 to 20 and 21 to 24, respectively) for the control experiment.

Then, each of the substrates of Example 2 and the control substrate was heated at 80° C. for 1 hour to immobilize each oligonucleotide strand thereonto.

The nucleic acid sequences of the oligonucleotide strands 5 to 8 immobilized on the plastic substrates are shown below.

```
Oligonucleotide Strand 5 (RING1-TP(a)):
                                 (SEQ ID NO: 17)
5'-AGATYGCGATCYCCTGTCCA-3'

Oligonucleotide Strand 6 (G1SKR):
                                 (SEQ ID NO: 18)
5'-CCAACCCARCCATTRTACA-3'

Oligonucleotide Strand 7 (COG2F):
                                 (SEQ ID NO: 19)
5'-CARGARBCNATGTTYAGRTGGATGAG-3'

Oligonucleotide Strand 8 (RING2AL-TP rc):
                                 (SEQ ID NO: 20)
5'-AGATYGCGATCWCCCTCCCA-3'

IUB Codes (Code of International Union of
Biochemistry). R = A or G; B = C, G or T;
Y = C or T; D = A, G or T; K = G or T;
H = A, C or T; M = A. or C; V = A, C or G;
S = G or C; W = A or T; N = any base.
```

Then, 59 µL of the target nucleic acid sequence, 8.0 µL of 10×MPEX buffer A, 8.0 µL of 10×KOD-Plus buffer (TOYOBO CO., LTD.), 0.80 µL of 0.1 mM biotinylated dUTP, 0.8 µL of 0.1 mM dATP, 0.8 µL of 0.1 mM dCTP, 0.8 µL of 0.1 mM dGTP, and 2 µL of KOD-Plus (TOYOBO CO., LTD.) were mixed to prepare a mixture solution, which was in turn added onto each substrate of Example 2. A reaction system in the substrate was heated at 95° C. for 8 minutes, thereby dissociating the double-stranded nucleic acid sequence into single strands through heat denaturation.

Next, the substrate was covered with cover glass and placed in a hermetically sealed container (10 cm×15 cm×3 cm) having the interior moistened with 200 µL of a 0.25 M phosphate buffer (pH 8.5). The reaction system was reacted at 56° C. for 90 minutes.

Next, the cover glass was removed, and the substrate was washed. Then, 8 µL of an alkaline phosphatase-labeled streptavidin with a concentration of 0.01 mg/mL, 8.0 µL of 10×MPEX buffer A, 40 µl, of 2×MPEX buffer B, and 24 µL of sterilized water were mixed in these proportions to prepare a mixture solution, which was in turn added to the plastic substrate.

Next, the substrate was covered with cover glass and placed in a hermetically sealed container (10 cm×15 cm×3 cm) having the interior moistened with 200 µl of a 0.25 M phosphate buffer (pH 8.5). The reaction system was reacted at 37° C. for 30 minutes. Then, the substrate was washed and then immersed in a BCIP/NBT solution (BCIP/NBT Phosphatase Substrate (1-Component System) (KPL)). The reaction system was reacted at 37° C. for 30 minutes, and the substrate was washed to produce spots with a bluish-purple color.

Color signals were captured as color images into a personal computer using an image scanner (PIXUS MP470 manufactured by Canon Inc.). Color intensity was digitized using image analysis software (Daredemo DNA Array analysis software manufactured by SUMITOMO BAKELITE Co., Ltd.).

In Example 2, the detection experiment was conducted at 7 levels of target nucleic acid sequence concentrations of 0, $10^0$, $10^1$, $10^2$, $10^4$, $10^6$, and $10^8$ copies/µL. Likewise, the control experiment using only one kind of oligonucleotide was conducted at 7 levels of target nucleic acid sequence concentrations of 0, $10^0$, $10^1$, $10^2$, $10^4$, $10^6$, and $10^8$ copies/µL.

Figure 9:
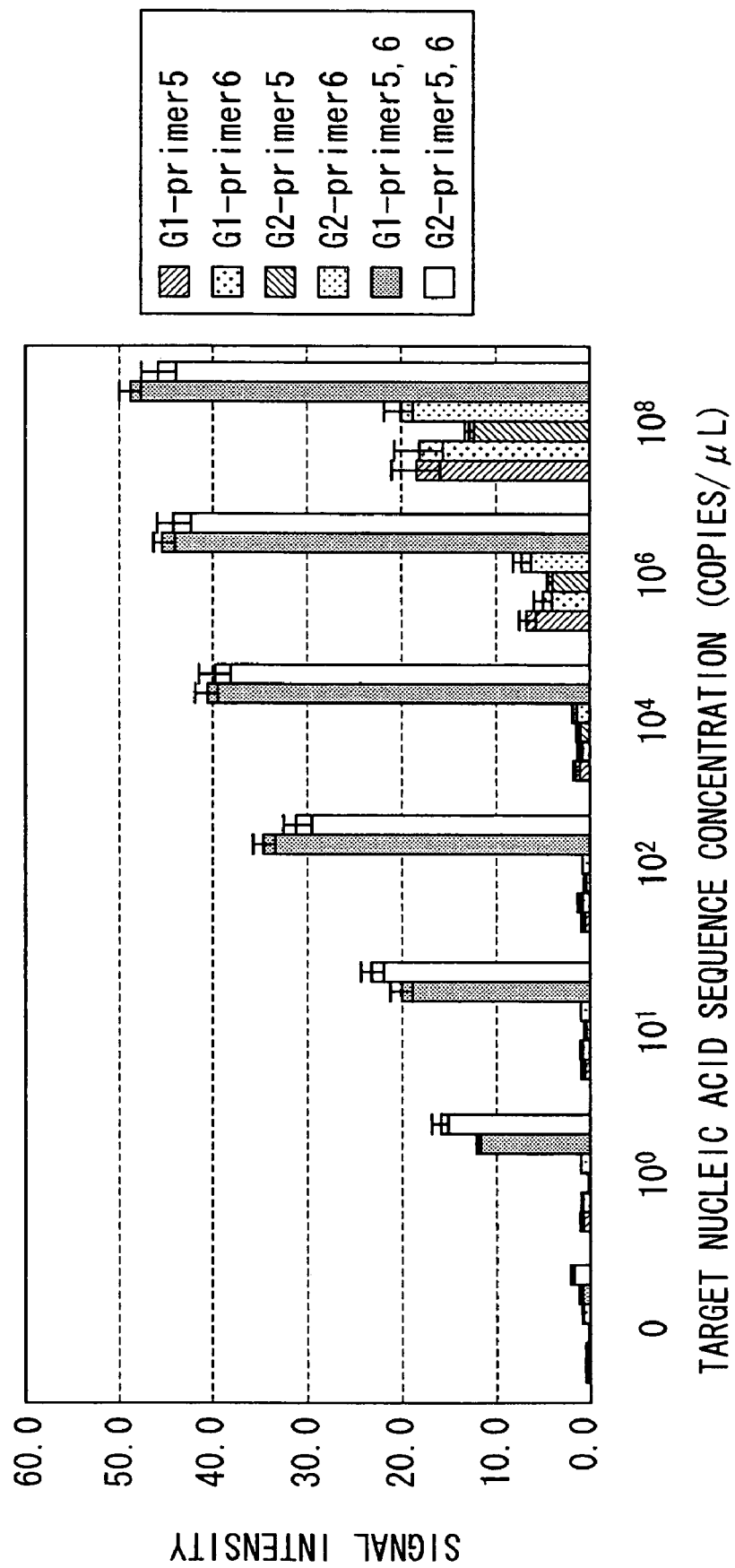
FIG. 9 is a graph for showing results in Example 2.

The amount of color signals was then compared between Example 2 and the control experiment at each of the concentrations. The comparison results are shown in FIG. 9. As a result, the control experiment using only one kind of oligonucleotide strand required the target nucleic acid sequence concentration of $10^6$ copies/µL or higher for detecting the target nucleic acid sequence, as can been seen from FIG. 9.

By contrast, in Example 2 using two kinds of oligonucleotides, wherein an elongation reaction product forms a cross-linked structure, the target nucleic acid sequence concentration of $10^0$ copies/µL or higher was enough to detect the target nucleic acid sequence. Thus, Example 2 achieved detection even for an exceedingly low concentration of a target nucleic acid sequence.

What is claimed is:

1. A method of nucleic acid sequence detection for detecting the presence of a particular target nucleic acid sequence to be detected in a sample, the method comprising:

a design step of designing first and second oligonucleotide strands in advance such that the second oligonucleotide strand has a complementary nucleic acid sequence to an elongation reaction product dissociated from a duplex formed through elongation reaction using the first oligonucleotide strand as a primer and the target nucleic acid sequence as a template after complementary binding of the target nucleic acid sequence and the first oligonucleotide strand;

an immobilization step of anchoring the first and second oligonucleotide strands onto a substrate by immobilizing the 5'-ends thereof onto the substrate;

a first elongation reaction step of complementarily binding the first oligonucleotide strand to the target nucleic acid sequence and performing first elongation reaction using the first oligonucleotide strand as a primer and the target nucleic acid sequence as a template;

a first dissociation step of dissociating, from the target nucleic acid sequence, the first elongation reaction product extended in the first elongation reaction step;

a first cross-linking step of binding the dissociated first elongation reaction product to the second oligonucleotide strand to form a cross-linked structure between the first and second oligonucleotide strands;

a second elongation reaction step of performing second elongation reaction using the second oligonucleotide strand as a primer and the first elongation reaction product as a template;

a second dissociation step of dissociating therefrom the second elongation reaction product extended in the second elongation reaction step;

a second cross-linking step of performing the first elongation reaction step to the second dissociation step on a plurality of the first and second oligonucleotide strands and binding a first oligonucleotide strand different from the first oligonucleotide strand to the dissociated second elongation reaction product to form a cross-linked structure between the second and first oligonucleotide strands;

a repetitive cross-linking step of repeating the first and second cross-linking steps between a plurality of the first and second oligonucleotide strands;

a reticulated space formation step of forming a reticulated space by the repetitive cross-linking step, wherein a plurality of the cross-linked structures are intertwined with each other;

a capture step of capturing a ligand within the reticulated space through physical adsorption;

a coloring step of causing the captured ligand to color with an active substance reactive to the ligand; and a detection step of detecting a color signal derived from the coloring to detect the target nucleic acid sequence.

2. The method of nucleic acid sequence detection according to claim 1, further comprising:

a third elongation reaction step of binding the second elongation reaction product dissociated in the second dissociation step to a third oligonucleotide strand designed such that the third oligonucleotide strand has a complementary nucleic acid sequence to the second elongation reaction product and performing third elongation reaction using the third oligonucleotide strand as a primer and the second elongation reaction product as a template;

a third dissociation step of dissociating, from the second elongation reaction product, the third elongation reaction product extended in the third elongation reaction step;

a third cross-linking step of binding a first oligonucleotide strand different from the first oligonucleotide strand to the dissociated third elongation reaction product to form a cross-linked structure between the third and first oligonucleotide strands; and a repetitive cross-linking step of repeating the first, second, and third cross-linking steps between a plurality of the first, second, and third oligonucleotide strands.

3. The method of nucleic acid sequence detection according to claim 2, further comprising a hybridization step of setting the temperature after the repetitive cross-linking step to a hybridization temperature for the oligonucleotide strands.

4. The method of nucleic acid sequence detection according to claim 1, further comprising a hybridization step of setting the temperature after the repetitive cross-linking step to a hybridization temperature for the oligonucleotide strands.

5. The method of nucleic acid sequence detection according to claim 1, wherein the ligand is one member selected from the group consisting of biotin, avidin, antigens, antibodies, hapten, oligonucleotides, and enzymes.

6. The method of nucleic acid sequence detection according to claim 1, wherein the ligand is one member selected from the group consisting of biotinylated enzymes, avidinylated enzymes, streptavidinylated enzymes, enzyme labels, and enzyme-labeled oligonucleotides.

7. The method of nucleic acid sequence detection according to claim 1, wherein the active substance is one member selected from the group consisting of enzyme-labeled receptors, fluorescent substance-labeled receptors, and substrates.

8. The method of nucleic acid sequence detection according to claim 1, wherein the substrate has, on the surface thereof, a layer comprising a hydrophilic polymer as well as a functional group reactive to an amino group.

9. A method of nucleic acid sequence detection for detecting the presence of a particular target nucleic acid sequence to be detected in a sample, the method comprising:

designing first and second oligonucleotide strands in advance such that the second oligonucleotide strand has a complementary nucleic acid sequence to an elongation reaction product dissociated from a duplex formed through elongation reaction using the first oligonucleotide strand as a primer and the target nucleic acid sequence as a template after complementary binding of the target nucleic acid sequence and the first oligonucleotide strand;

immobilizing a plurality of the designed first and second oligonucleotide strands onto a substrate;

mixing the sample containing the target nucleic acid sequence with a ligand as a constituent of a chromogenic substance to prepare a mixture solution;

adding the mixture solution to a reaction system on the substrate and setting the temperature of the reaction system to a heat denaturation temperature at which the target nucleic acid sequence is heat-denatured;

setting the temperature of the reaction system to a first elongation reaction temperature at which the first oligonucleotide strand complementarily binds to the target nucleic acid sequence for first elongation reaction;

setting the temperature of the reaction system to a first dissociation temperature at which the first elongation reaction product is dissociated from the first duplex formed through the first elongation reaction;

setting the temperature of the reaction system to a second elongation reaction temperature at which the dissociated first elongation reaction product complementarily binds to the second oligonucleotide strand for second elongation reaction;

setting the temperature of the reaction system to a second dissociation temperature at which the second elongation reaction product is dissociated from the second duplex formed through the second elongation reaction;

setting the temperature of the reaction system to a temperature at which the dissociated second elongation reaction product complementarily binds to the first oligonucleotide strand;

capturing the ligand within a reticulated space formed on the substrate;

adding, onto the substrate, an active substance as another constituent of the chromogenic substance and setting the temperature to a temperature for reaction with the ligand; and detecting a color signal derived from coloring by the chromogenic substance.

10. The method of nucleic acid sequence detection according to claim 9, wherein the ligand is one member selected from the group consisting of biotin, avidin, antigens, antibodies, hapten, oligonucleotides, and enzymes.

11. The method of nucleic acid sequence detection according to claim 9, wherein the ligand is one member selected from the group consisting of biotinylated enzymes, avidinylated enzymes, streptavidinylated enzymes, enzyme labels, and enzyme-labeled oligonucleotides.

12. The method of nucleic acid sequence detection according to claim 9, wherein the active substance is one member selected from the group consisting of enzyme-labeled receptors, fluorescent substance-labeled receptors, and substrates.

13. The method of nucleic acid sequence detection according to claim 9, wherein the substrate has, on the surface thereof, a layer comprising a hydrophilic polymer as well as a functional group reactive to an amino group.

14. A method of detecting a target nucleic acid when present in a sample, comprising:

contacting the sample and a substrate, the substrate having a plurality of first and second oligonucleotides immobilized on the substrate, the first oligonucleotide comprising a sequence complementary to a sequence of the target nucleic acid and the second oligonucleotide comprising a sequence complementary to a sequence of a first elongation reaction product;

when the target nucleic acid is present in the sample:

forming a reticulated space from a plurality of intertwined, cross-linked structures, wherein forming the reticulated space comprises performing the following a plurality of times:

binding the first oligonucleotide to the target nucleic acid;

performing an elongation reaction using the first oligonucleotide as a primer and the target nucleic acid as a template to obtain the first elongation reaction product;

dissociating the first elongation reaction product from the target nucleic acid;

binding the first elongation reaction product to the second oligonucleotide to form a cross-linked structure between the first and second oligonucleotides;

performing an elongation reaction using the second oligonucleotide as a primer and the first elongation reaction product as a template to obtain a second elongation reaction product;

dissociating the second elongation reaction product from the first elongation reaction product;

binding the second elongation reaction product to a different first oligonucleotide to form a cross-linked structure between the first oligonucleotide and the second oligonucleotide; and performing an elongation reaction using the first oligonucleotide as a primer and the second elongation reaction product as a template;

capturing a ligand within the reticulated space; and producing a detectable signal indicative of the presence of the target nucleic acid in the sample by way of the captured ligand and an active substance.

15. The method of claim 14, wherein the ligand is captured within the reticulated space by physical adsorption.

16. A method of detecting a target nucleic acid when present in a sample, comprising:

mixing the sample with a ligand to prepare a mixture;

applying the mixture to a substrate, the substrate having a plurality of first and second oligonucleotides immobilized on the substrate, the first oligonucleotide comprising a sequence complementary to a sequence of the target nucleic acid and the second oligonucleotide comprising a sequence complementary to a sequence of a first elongation reaction product;

when the target nucleic acid is present in the sample:

heat denaturing the target nucleic acid;

forming a reticulated space from a plurality of intertwined, cross-linked structures, wherein forming the reticulated space comprises performing the following a plurality of times:

binding the first oligonucleotide to the target nucleic acid;

performing an elongation reaction using the first oligonucleotide as a primer and the target nucleic acid as a template to obtain the first elongation reaction product;

dissociating the first elongation reaction product from the target nucleic acid;

binding the first elongation reaction to the second oligonucleotide to form a cross-linked structure between the first and second oligonucleotides;

performing an elongation reaction product using the second oligonucleotide as a primer and the first elongation reaction product as a template to obtain a second elongation reaction product;

dissociating the second elongation reaction product from the first elongation reaction product;

binding the second elongation reaction product to a different first oligonucleotide to form a cross-linked structure between the first oligonucleotide and the second oligonucleotide; and performing an elongation reaction using the first oligonucleotide as a primer and the second elongation reaction product as a template;

capturing the ligand within the reticulated space;

adding an active substance that binds to or reacts with the ligand; and producing a detectable signal indicative of the presence of the target nucleic acid in the sample by way of the ligand and the active substance.

17. The method of claim 16, wherein the ligand is captured within the reticulated space by physical adsorption.

* * * * *

SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 1
atccgtgaca gaagagacag a                                              21

<210> SEQ ID NO 2
<211> LENGTH: 6
<212> TYPE: DNA
<213> ORGANISM: Artificial Sequence
<220> FEATURE:
<223> OTHER INFORMATION: oligonucleotide strand

<400> SEQUENCE: 2 acggat                                                                6

<210> SEQ ID NO 3
<211> LENGTH: 6
<212> TYPE: DNA
<213> ORGANISM: Artificial Sequence
<220> FEATURE:
<223> OTHER INFORMATION: oligonucleotide strand; sequence portion of
      SEQ ID No. 1

<400> SEQUENCE: 3 atccgt                                                                6

<210> SEQ ID NO 4
<211> LENGTH: 6
<212> TYPE: DNA
<213> ORGANISM: Artificial Sequence
<220> FEATURE:
<223> OTHER INFORMATION: oligonucleotide strand

<400> SEQUENCE: 4 tctgtc                                                                6

<210> SEQ ID NO 5
<211> LENGTH: 6
<212> TYPE: DNA
<213> ORGANISM: Artificial Sequence
<220> FEATURE:
<223> OTHER INFORMATION: oligonucleotide strand; sequence portion of
      SEQ ID No:1

<400> SEQUENCE: 5 gacaga                                                                6

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
agacagataa gtcagtgcct a                                              21

<210> SEQ ID NO 7
<211> LENGTH: 15
<212> TYPE: DNA
<213> ORGANISM: Artificial Sequence
<220> FEATURE:
<223> OTHER INFORMATION: oligonucleotide strand; DNA/RNA

<400> SEQUENCE: 7 cuga cuuaucuguc u                                                    15
```

```
<210> SEQ ID NO 8
<211> LENGTH: 6
<212> TYPE: RNA
<213> ORGANISM: Artificial Sequence
<220> FEATURE:
<223> OTHER INFORMATION: oligonucleotide strand; sequence portion of
      SEQ ID No:7

<400> SEQUENCE: 8 cugucu                                                                    6

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct; Primer 1 (COG1F)
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: y is c or t

<400> SEQUENCE: 9
cgytggatgc gnttycatga                                                    20

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct; Primer 2 (G1-SKR)
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (15)..(15)
<223> OTHER INFORMATION: r is a or g

<400> SEQUENCE: 10
ccaacccarc cattrtaca                                                     19

<210> SEQ ID NO 11
<211> LENGTH: 26
<212> TYPE: DNA
<213> ORGANISM: Artificial Sequence
<220> FEATURE:
<223> OTHER INFORMATION: Synthetic Construct; Primer 3 (COG2F)
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (7)..(7)
<223> OTHER INFORMATION: b is c, g or t
<220> FEATURE:
<221> NAME/KEY: misc_feature
<222> LOCATION: (9)..(9)
```

```
<223> OTHER INFORMATION: n is a, c, g, or t
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (18)..(18)
<223> OTHER INFORMATION: r is a or g

<400> SEQUENCE: 11
cargarbcna tgttyagrtg gatgag                                              26

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct; Primer 4 (G2-SKR)
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: r is a or g
<220> FEATURE:
<221> NAME/KEY: misc_feature
<222> LOCATION: (12)..(12)
<223> OTHER INFORMATION: h is a
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: r is a or g

<400> SEQUENCE: 12
ccrccngcat rhccrttrta cat                                                 23

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide Strand 1 (G1SKF)
<220> FEATURE:
<221> NAME/KEY: misc_feature
<222> LOCATION: (11)..(11)
<223> OTHER INFORMATION: y is c or t

<400> SEQUENCE: 13
ctgcccgaat tygtaaatga                                                     20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide Strand 2 (G1-1')

<400> SEQUENCE: 14
ccaacaaaca tggatggcac                                                     20

<210> SEQ ID NO 15
```

```
<211> LENGTH: 20
<212> TYPE: DNA
<213> ORGANISM: Artificial Sequence
<220> FEATURE:
<223> OTHER INFORMATION: Oligonucleotide Strand 3 (RING2AL-TP)
<220> FEATURE:
<221> NAME/KEY: misc_feature
<222> LOCATION: (9)..(9)
<223> OTHER INFORMATION: s is g or c
<220> FEATURE:
<221> NAME/KEY: misc_feature
<222> LOCATION: (16)..(16)
<223> OTHER INFORMATION: r is a or g

<400> SEQUENCE: 15
tgggagggsg atcgcratct                                               20

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide Strand 4 (G2SKRrc)
<220> FEATURE:
<221> NAME/KEY: misc_feature
<222> LOCATION: (6)..(6)
<223> OTHER INFORMATION: y is c or t
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (12)..(12)
<223> OTHER INFORMATION: d is a, g or t
<220> FEATURE:
<221> NAME/KEY: misc_feature
<222> LOCATION: (13)..(13)
<223> OTHER INFORMATION: y is c or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: y is c or t

<400> SEQUENCE: 16
atgtayaayg gdyatgcngg ygg                                           23

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide Strand 5 (RING1-TP(a))
<220> FEATURE:
<221> NAME/KEY: misc_feature
<222> LOCATION: (5)..(5)
<223> OTHER INFORMATION: y is c or t
<220> FEATURE:
<221> NAME/KEY: misc_feature
<222> LOCATION: (11)..(11)
<223> OTHER INFORMATION: y is c or t

<400> SEQUENCE: 17
agatygcgat cycctgtcca                                               20

<210> SEQ ID NO 18
<211> LENGTH: 19
<212> TYPE: DNA
<213> ORGANISM: Artificial Sequence
<220> FEATURE:
```

```
<223> OTHER INFORMATION: Oligonucleotide Strand 6 (G1SKR)
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (15)..(15)
<223> OTHER INFORMATION: r is a or g

<400> SEQUENCE: 18
ccaacccarc cattrtaca                                                  19

<210> SEQ ID NO 19
<211> LENGTH: 26
<212> TYPE: DNA
<213> ORGANISM: Artificial Sequence
<220> FEATURE:
<223> OTHER INFORMATION: Oligonucleotide Strand 7 (COG2F)
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (7)..(7)
<223> OTHER INFORMATION: b is c, g or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (18)..(18)
<223> OTHER INFORMATION: r is a or g

<400> SEQUENCE: 19
cargarbcna tgttyagrtg gatgag                                          26

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide Strand 8 (RING2AL-TP rc)
<220> FEATURE:
<221> NAME/KEY: misc_feature
<222> LOCATION: (5)..(5)
<223> OTHER INFORMATION: y is c or t
<220> FEATURE:
<221> NAME/KEY: misc_feature
<222> LOCATION: (11)..(11)
<223> OTHER INFORMATION: w is a or t

<400> SEQUENCE: 20
agatygcgat cwccctccca                                                 20

<210> SEQ ID NO 21
<211> LENGTH: 6
<212> TYPE: DNA
<213> ORGANISM: Artificial Sequence
<220> FEATURE:
<223> OTHER INFORMATION: oligonucleotide strand

<400> SEQUENCE: 21
```

```
                                              -continued
taggca                                                                               6

<210> SEQ ID NO 22
<211> LENGTH: 6
<212> TYPE: DNA
<213> ORGANISM: Artificial Sequence
<220> FEATURE:
<223> OTHER INFORMATION: oligonucleotide strand

<400> SEQUENCE: 22 agacag                                                                               6
```